(12) United States Patent
Baghbaderani et al.

(10) Patent No.: US 8,093,053 B2
(45) Date of Patent: Jan. 10, 2012

(54) METHODS AND COMPOSITIONS FOR CULTURING OF NEURAL PRECURSOR CELLS

(75) Inventors: Behnam A. Baghbaderani, Calgary (CA); Arindom Sen, Calgary (CA); Michael S. Kallos, Calgary (CA); Leo A. Behie, Calgary (CA)

(73) Assignee: UTI Limited Partnership, Calgary (CA)

( * ) Notice: Subject to any disclaimer, the term of this patent is extended or adjusted under 35 U.S.C. 154(b) by 0 days.

(21) Appl. No.: 12/405,736

(22) Filed: Mar. 17, 2009

(65) Prior Publication Data

US 2009/0233360 A1     Sep. 17, 2009

Related U.S. Application Data

(60) Provisional application No. 61/037,253, filed on Mar. 17, 2008.

(51) Int. Cl.
| | |
|---|---|
| C12N 5/00 | (2006.01) |
| C12N 5/0789 | (2010.01) |
| C12N 5/079 | (2010.01) |
| C12M 3/00 | (2010.01) |
| C12N 5/02 | (2010.01) |

(52) U.S. Cl. ............ 435/404; 435/368; 435/283.1; 435/394; 435/325; 435/377; 435/383

(58) Field of Classification Search .................. None
See application file for complete search history.

(56) References Cited

U.S. PATENT DOCUMENTS 5,817,773 A * 10/1998 Wilson et al. .............. 530/399
6,238,922 B1 * 5/2001 Uchida ...................... 435/380

FOREIGN PATENT DOCUMENTS

WO     WO 2007/002086       1/2007

OTHER PUBLICATIONS

Sen et al Masters Abs Int. 39, 391 pages, 1998.*
Wu et al. (Nature Neurosc 5: 1271-1278, 2002).*
Bachoud-Lévi et al., "Safety and tolerability assessment of intrastriatal neural allografts in five patients with Huntington's disease," *Exp. Neurol.*, 161:194-202, 2000.
Baghbaderani et al., "Expansion of human neural precursor cells in large-scale bioreactors for the treatment of neurodegenerative disorders," American Chemical Society and American Institute of Chemical Engineers, published on wed Apr. 2, 2008.
Carpenter et al., "In vitro expansion of a multipotent population of human neural progenitor cells," *Exp. Neurol.*, 158:265-278, 1999.
Dunnett and Rosser, "Cell therapy in Huntington's disease," *NeuroRx.*, 1:394-405, 2004.
Dunnett and Rosser, "Cell transplantation for Huntington's disease Should we continue?," *Brain Res. Bull.*, 72:132-147, 2007.
Gilbertson et al., "Scaled-up production of mammalian neural precursor cell aggregates in computer-controlled suspension bioreactors," *Biotechnol. Bioeng.*, 94:783-92, 2006.
Kallos and Behie, "Inoculation and growth conditions for high-cell-density expansion of mammalian neural stem cells in suspension bioreactors," *Biotechnol. Bioeng.*, 63:473-483, 1999.
Kallos et al., "Extended serial passaging of mammalian neural stem cells in suspension bioreactors," *Biotechnol. Bioeng.*, 65:589-599, 1999.
Kallos et al., "Large-scale expansion of mammalian neural stem cells: a review," *Med. Biol. Eng. Comput.*, 41:271-282, 2003.
Kopyov et al., "Safety of intrastriatal neurotransplantation for Huntington's disease patients," *Exp. Neurol.*, 149:97-108, 1998.
Mendez et al., "Cell type analysis of functional fetal dopamine cell suspension transplants in the striatum and substantia nigra of patients with Parkinson's disease," *Brain*, 128:1498-1510, 2005.
Mendez et al., "Simultaneous intrastriatal and intranigral fetal dopaminergic grafts in patients with Parkinson disease: a pilot study. Report of three cases," *J. Neurosurg.*, 96:589-596, 2002.
Mukhida et al., "Co-grafting with bioreacter-expanded human neural precursor cells enhances survival of fetal dopaminergic transplants in Hemiparkinsonian rodents," *Exp. Neurol.*, 198:582, 2006, Abstract.
Mukhida et al., "Spinal GABAergic transplants attenuate mechanical allodynia in a rat model of neuropathic pain," *Stem Cells*, 25:2874-2885, 2007.
Philpott et al., "Neuropsychological functioning following fetal striatal transplantation in Huntington's chorea: three case presentations," *Cell Transplant.*, 6:203-212, 1997, Abstract.
Rosser et al., "Unilateral transplantation of human primary fetal tissue in four patients with Huntington's disease: NEST-UK safety report ISRCTN No. 36485475," *J. Neurol. Neurosurg. Psychiatry.*, 73:678-685, 2002.
Sen et al., "Effects of hydrodynamic on extended cultures of mammalian neural stem cell aggregates in suspension culture," *Ind Eng. Chem. Res.*, 40:5350-5357, 2001.
Sen et al., "Expansion of mammalian neural stem cells in bioreactors: effect of power input and medium viscosity," *Brain Res. Dev. Brain Res.*, 134:103-113, 2002.
Sen et al., "Passaging protocols for mammalian neural stem cells in suspension bioreactors," *Biotechnol. Prog.*, 18:337-345, 2002.
Storch and Schwartz, "Neural stem cells and neurodegeneration," *Curr. Opin. Investig. Drugs*, 3:774-781, 2002.
Storch et al., "Long-term proliferation and dopaminergic differentiation of human mesencephalic neural precursor cells," *Exp. Neurol.*, 170:317-325, 2001.
Suzuki et al., "Mitotic and neurogenic effects of dehydroepiandrosterone (DHEA) on human neural stem cell cultures derived from the fetal cortex," *Proc. Natl. Acad. Sci. USA*, 101:3202-3207, 2004.
Svendsen et al., "A new method for the rapid and long term growth of human neural precursor cells," *J. Neurosci. Methods*, 85:141-152, 1998.

(Continued)

*Primary Examiner* — Daniel E Kolker
*Assistant Examiner* — Aditi Dutt
(74) *Attorney, Agent, or Firm* — Fulbright & Jaworski

(57) ABSTRACT

The present invention provides methods and compositions for the propagation and expansion of neural precursor cells (NPCs). NPCs may be used in the clinical implementation of stem cell therapy to treat disorders such as Parkinson's disease, Huntington's disease, neuropathic pain and other diseases of the central nervous system. The large-scale production of NPCs in bioreactors allows for the generation of clinical quantities of these cells.

38 Claims, 10 Drawing Sheets

OTHER PUBLICATIONS

Vescovi et al., "Isolation and cloning of multipotential stem cells from the embryonic human CNS and establishment of transplantable human neural stem cell lines by epigenetic stimulation," *Exp. Neurol.*, 156:71-83, 1999.

Youn et al., "Large-scale expansion of mammary epithelial stem cell aggregates in suspension bioreactors," *Biotechnol. Prog.*, 21:984-993, 2005.

Youn et al., "Scale-up of breast cancer stem cell aggregate cultures to suspension bioreactors," *Biotechnol, Prog.*, 22:801-810, 2006.

Baghbaderani et al., "Bioreactor expansion of human neural precursor cells in serum-free media retains neurogenic potential," *Biotechnology and Bioengineering*, 105:823-833, 2010.

* cited by examiner

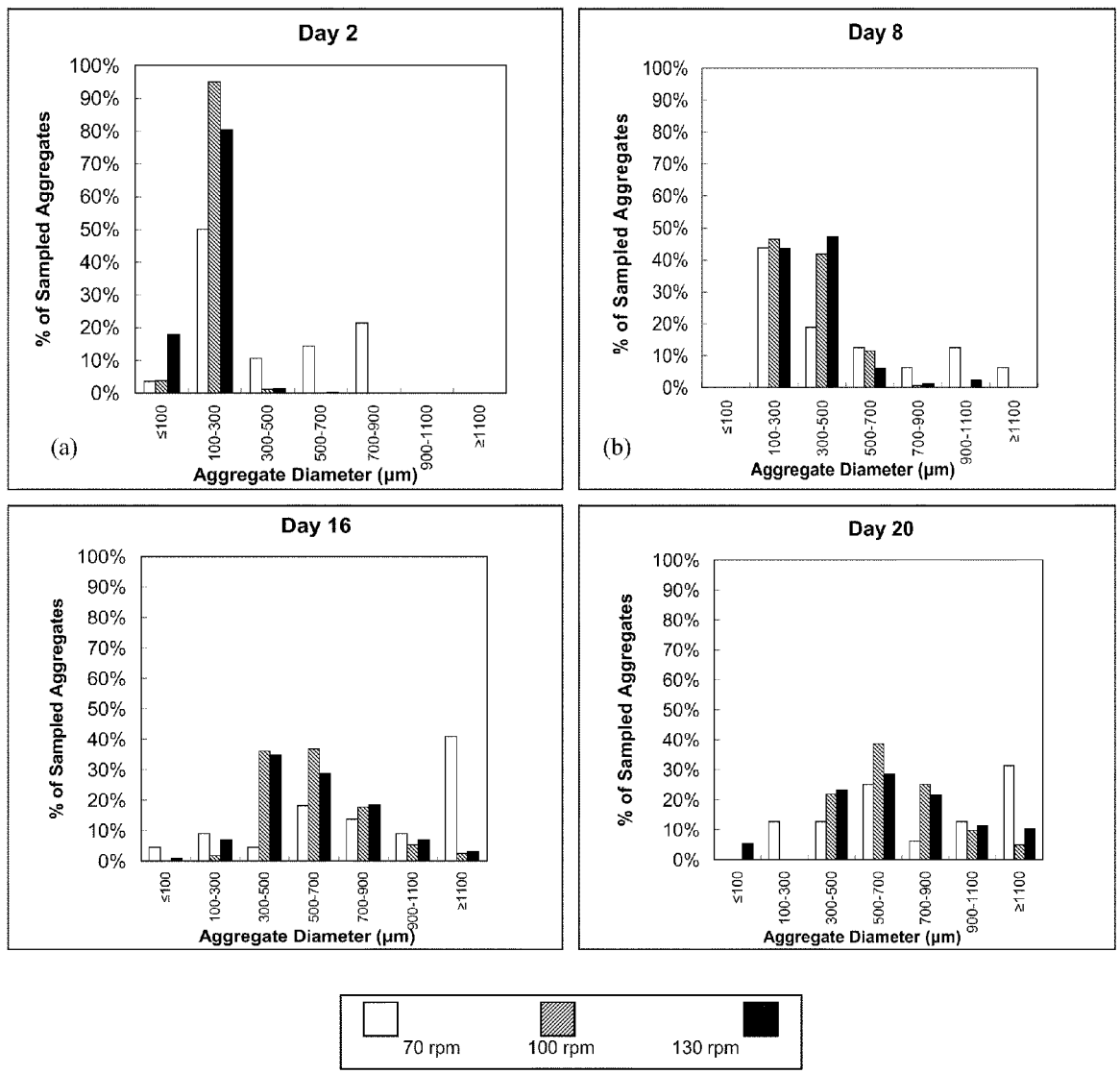
FIG. 7A-D

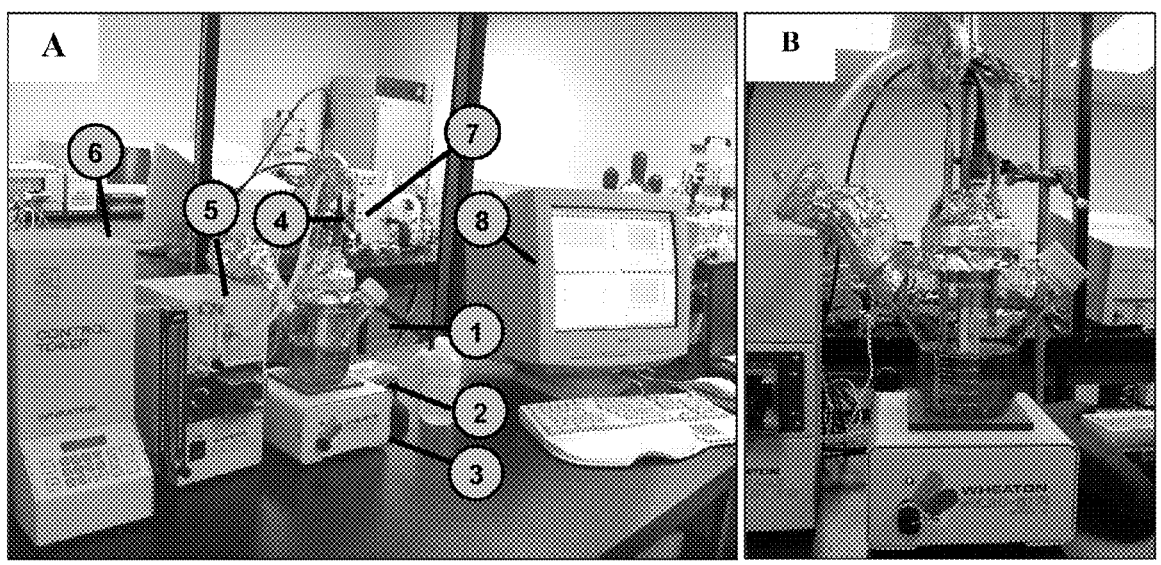
FIG. 8A-B

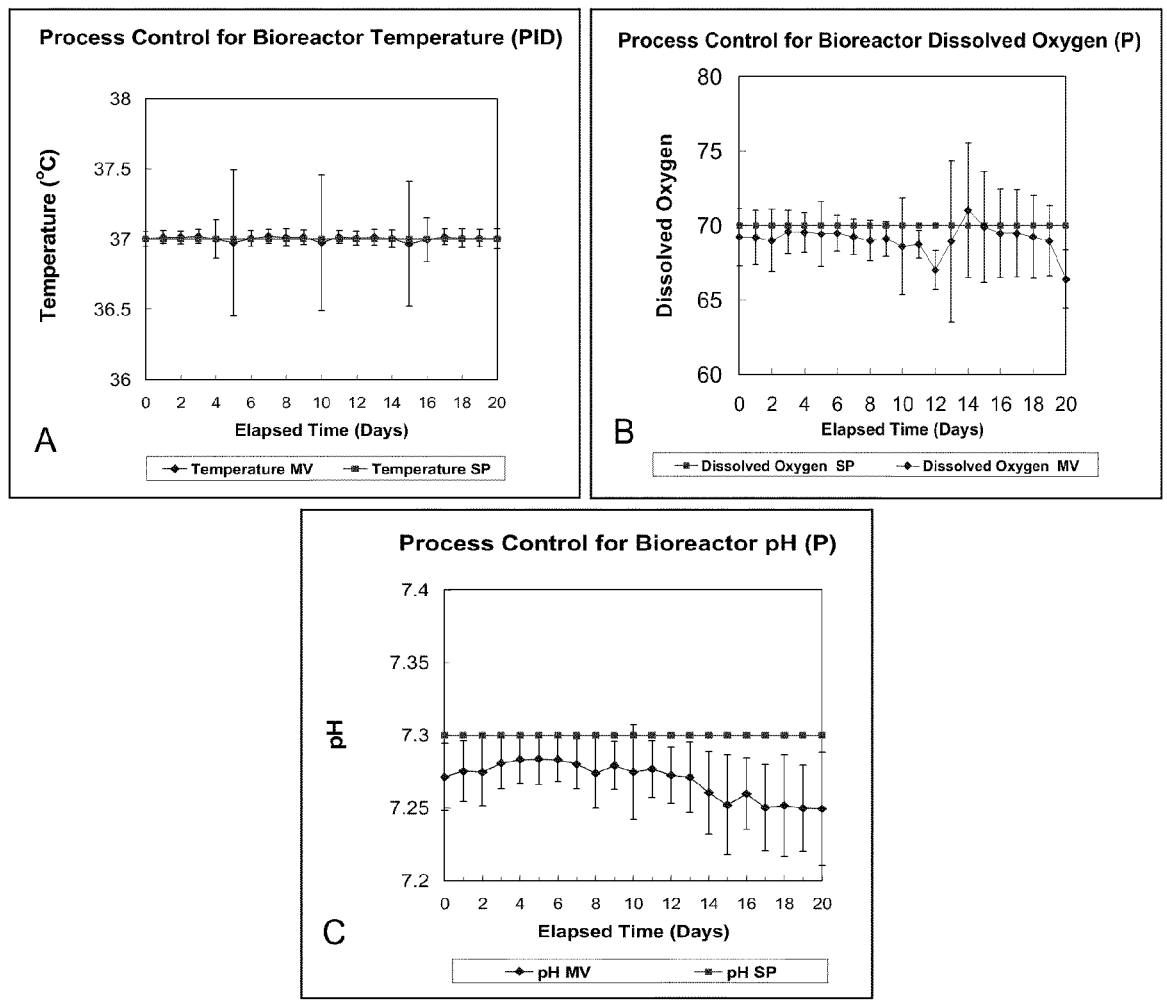
FIG. 9A-C

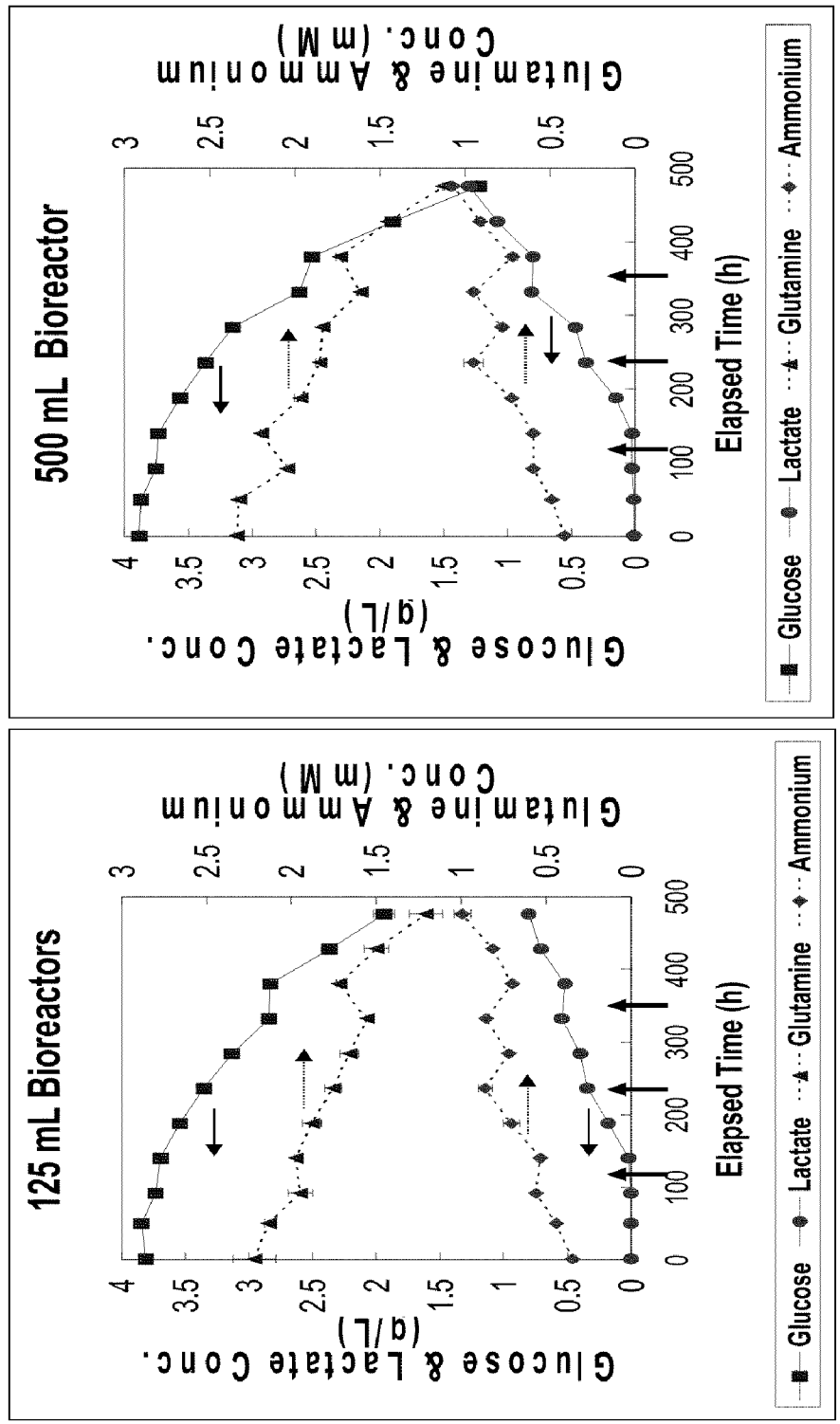
FIG. 10A-B

METHODS AND COMPOSITIONS FOR CULTURING OF NEURAL PRECURSOR CELLS

The present invention claims benefit of priority to U.S. Provisional Application Ser. No. 61/037,253, filed Mar. 17, 2008, the entire contents of which are hereby incorporated by reference.

BACKGROUND OF THE INVENTION

1. Field of the Invention

The present invention relates generally to the fields of neurobiology, cell biology, and stem cell bioengineering. More particularly, it concerns methods and compositions for culturing of neuronal precursor cells, including large scale methods.

2. Description of the Related Art

Central nervous system disorders such as Parkinson's disease (PD) and Huntington's disease (HD) affect millions of individuals in North America and cost health care systems over $250 billion/year (Kallos et al., 2003). PD and HD are neurodegenerative disorders characterized by the selective and gradual loss of dopamine (DA)-producing neurons (DAergic neurons) and γ-aminobutyric acid (GABA)-producing neurons (GABAergic neurons), respectively (Storch and Schwarz, 2002). Conventional treatment methods for these disorders are focused on the administration of drugs to alleviate symptoms. However, these medical therapies do not replace the lost cells and become ineffective over time.

Previous studies have shown that cell replacement therapy using fetal tissue may be a viable treatment option for PD (Freed et al., 1992; Lindvall et al., 1990; Lindvall et al., 1994; Piccini et al., 1999; Piccini et al., 2000) and HD (Bachoud-Levi et al., 2000; Bachoud-Levi et al., 2006; Bachoud-Levi et al., 2000; Philpott et al., 1997). In the case of PD, two double-blind studies performed by the National Institutes of Health (NIH) found that the transplantation of fetal DA neurons into the brain of PD patients resulted in modest functional benefits but also caused undesirable side effects (Freed et al., 2001; Olanow et al., 2003). However, recently, Mendez et al. (Mendez et al., 2002; Mendez et al., 2005) demonstrated that a new transplantation procedure with a multiple-graft strategy and placement of cells in both the caudate and substantia nigra of the brain benefited PD patients without the side-effects previously reported. In the case of HD, the results of transplantation of fetal striatal tissue into the striatum of HD patients showed that fetal tissue can be isolated for use in the treatment of HD and that neurological implantation of the isolated cells is safe (Bachoud-Levi et al., 2000; Kopyov et al., 1998; Rosser et al., 2002), and the transplantation of these cells may have clinical benefits with respect to motor and cognitive outcomes (Bachoud-Levi et al., 2000; Philpott et al., 1997; Dunnett and Rosser, 2007).

Despite these encouraging results, the lack of fetal tissue availability may ultimately limit the clinical utility of this treatment approach. For example, reversal of symptoms in a single PD patient typically requires transplantation of primary tissue procured from 5-10 fetuses (Storch and Schwarz, 2002; Dunnett and Rosser, 2004). This issue becomes very pronounced when it is considered that there are millions of individuals who could benefit from this type of therapy. For this reason, together with the fact that fetal tissue is mired in ethical controversy, primary fetal cell therapy may not be of widespread clinical utility (Dunnett and Rosser, 2007). If cell replacement strategies are to become a routine therapeutic option for the treatment of neurodegenerative orders, then cell supply becomes a critical issue.

Human neural precursor cells (hNPCs) expanded in culture may represent a viable alternative to primary fetal tissue in clinical cell replacement strategies. Several studies have focused on development of growth medium and expansion of hNPCs in small tissue culture flasks (Carpenter et al., 1999; Storch et al., 2001; Suzuki et al., 2004; Svendsen et al., 1998; Vescovi et al., 1999). The inventors have also successfully modified an existing serum-free cell growth medium (PPRF-m4) that was originally developed for the expansion of murine neural precursor cells (mNPCs) to now support the expansion of fetal hNPCs. hNPCs obtained from different regions of the fetal brain including the forebrain, ventral mesencephalon, brain stem, and spinal cord have been expanded in both static culture and small-scale suspension bioreactors using this modified medium (PPRF-h2). hNPCs expanded in standard small-scale suspension bioreactors have been effectively used for transplantation studies in animal models of PD, HD, and neuropathic pain (Mukhida et al., 2007; Mukhida et al., 2006). The results showed that hNPCs expanded in small-scale bioreactors could be differentiated into a GABAergic phenotype which, when transplanted into lesioned animal models of neuropathic pain (Mukhida et al., 2007) and HD, resulted in significant functional recovery. Moreover, when these cells were co-grafted with fetal VM derived tissues, they enhanced the fetal dopaminergic neurons' survival following transplantation into a rat model of PD (Mukhida et al., 2006), suggesting a possible neurotrophic role for the bioreactor-expanded hNPCs.

In order for such cells to be approved for use in clinical settings, they must be generated in a reproducible manner under controlled, standard conditions. Small volume bioreactor methods make it difficult to incorporate the measuring probes necessary to monitor and properly control environmental parameters of the cell culture, and also do not permit the efficient production of sufficient cells to allow small quantities of primary hNPCs, isolated from a single fetus, to be expanded to clinical quantities. Thus, improved methods and compositions for large scale culturing of NPCs are needed.

SUMMARY OF THE INVENTION

Thus, in accordance with the present invention, there is provided a culture medium comprising, dissolved or dispersed in base culture media and water, the following components:
(a) nutrients;
(b) glutamine;
(c) glucose;
(d) heparin
(e) Hepes;
(f) recombinant human EGF;
(g) recombinant human bFGF;
(h) recombinant hLIF;
(i) DHEA;
(j) serum albumin;
(k) lipids; and
(m) a mixture of hormones comprising apo-transferrin, insulin, putrescine, selenium and progesterone.

The base culture medium may be DMEM. The nutrients may comprise Ham's F12 nutrient mixture. The serum albumin is human or bovine serum albumin, and in particular contains only isolated serum albumins, i.e., with no other significant amounts of serum components. The medium may be filter sterilized. The amounts of various components may be further defined as follow:

recombinant human EGF present at about 0.01 to about 100 µg/mL, at about 10 to about 40 µg/mL, or at about 20 µg/mL, recombinant human bFGF present at about 0.01 to about 100 µg/mL, at about 10 to about 40 µg/mL, or at about 20 µg/mL, recombinant hLIF present at about 0.01 to about 100 µg/mL, at about 5 to about 25 µg/mL, or at about 10 µg/mL DHEA present at about 0.01 to about 100 µmol/L, at 0.1 to about 5 µmol/L, or at about 1 µmol/L, apo-transferrin present at about 0.01 to about 100 mg/L, at about 10 to about 40 mg/L, or at about 25 mg/L, insulin present at about 0.01 to about 100 mg/L, at about 10 to about 40 mg/L, or at about 23 mg/L, putrescine present at about 0.01 to about 100 mg/L, at about 5 to about 20 mg/L, or at about 9 mg/L, selenium present at about 0.0001 to about 100 µM, at about 0.01 to about 1 µM, or at about 0.027 µM, progesterone present at about 0.0001 to about 100 µM, at about 0.01 to about 1 µM, or at about 0.018 µM.

In another embodiment, there is provided a bioreactor comprising at least one cell and a medium as described above. The cell may be a neural precursor cell. The container may be a dish, flask, vessel, bottle or multi-well plate.

In still another embodiment, there is provided a method of culturing a neural precursor cell (NPC) comprising the steps of (a) providing an isolated NPC or NPC-containing cell population in culture medium in a bioreactor; and (b) culturing said NPC or NPC-containing cell population under conditions that (i) produce cell aggregates having an average size of about 20-2000 µm in diameter after 4 days of culture, (ii) wherein said culture medium is maintained at a pH of about 7.0-7.8; and (iii) wherein said NPC or NPC-containing cell population is cultured in batch mode, semi-fed batch mode or perfusion mode. In particular, the culturing may comprise conditions that (i) produce cell aggregates having an average size of about 100-1000 µm in diameter after 5 days of culture, and (ii) wherein said culture medium is maintained at a pH of about 7.2-7.4. More than 50% of the cell aggregates may have a size of between about 300 to about 700 µM between days 8 and 20 of culture, and/or may have a mean size of between about 400 to about 600 µM. The bioreactor may be a dish, flask, vessel, bottle or multi-well plate. The oxygenation of said culture medium may be maintained at about 1-20% dissolved oxygen, at about 5-20% dissolved oxygen or in particular at about 14% dissolved oxygen. In certain embodiments, cells are grown in serum-free media, i.e., without whole serum, but including purified serum albumins.

The NPC may be a neural stem cell or neural progenitor cell. The NPC or NPC-containing population may be obtained from forebrain, ventral mesencephalon, brain stem or spinal cord. In particular, the forebrain population may be obtained from telencephalon. The NPC or NPC-containing population may be passaged 1, 2, 3, 4, 5, 6, 7, 8, 9, 10, 11, 12, or 13 times or more. The NPC or NPC-containing population may be maintained in culture for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 day. Also contemplated are days of culture of about 55, 60, 65, 70, 75, 80, 85, 90, 95, 100, 110, 120, 130 or 140 days or more. Other time ranges include 2-10 days, 10-20 days, 20-50 days, 50-100 days, 100-150 days, 50-150 days, or 2-150 days. The method may further comprise inducing differentiation of said NPC or NPC-containing population, such as into a CNS cell(s), an astrocyte(s) or a neuronal cell(s). The NPC or NPC-containing population may be maintained at about 75-95% viability, or more particularly 80-90% viability.

The NPC or NPC-containing population may be cultured in a stationary phase, or cultured in suspension with an agitation rate of greater than about 50 rpm and less than about 130 rpm. Agitation may be produced by a stir bar, an impeller or by movement of said bioreactor. Agitation may comprise culturing at about 80 to about 90 rpm, or in particular at about 85 rpm. The NPC or NPC-containing population may be cultured in about 0.1-5000 mL volume of culture medium, or in 100 mL, 200 mL, 500 mL, 1000 mL, 2000 mL, 3000 mL, 4000 mL or 5000 mL volumes of culture medium. Semi-batch fed mode may comprise replacement of 30-50% of said culture medium each 3-6 days. The cell-fold expansion per passage may be 5-50 for the first 140 days, or may be 10-40 for the first 140 days.

The embodiments in the Examples section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value, and may also be interpreted at +/−10% of a stated value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 7A-D: Aggregate Size Distribution Changes with Liquid Shear in 125 mL Bioreactors. Shown are aggregate size distributions (FIG. 7A) 2 days post-inoculation, (FIG. 7B) 8 days post-inoculation, (FIG. 7C) 16 days post-inoculation, and (FIG. 7D) 20 days post-inoculation at 70 rpm, 100 rpm, or 130 rpm. All data points represent the average of duplicate bioreactors.

FIGS. 8A-B: Photographs of 500 mL Computer-Controlled Suspension Bioreactor. (FIG. 8A) Experimental set-up for the 500 mL suspension bioreactor showing: (1) 500 mL suspension bioreactor, (2) heating pad, (3) stir plate, (4) gas inlets to the bioreactor connected to $O_2$, $CO_2$, $N_2$, and air gas cylinders via Wheaton pump, (5) Wheaton pump, (6) the control tower (Wheaton) connected to the dissolved oxygen (DO), pH, and temperature probes to monitor the level of each parameter, (7) DO, pH, and temperature probes, and (8) data acquisition computer. (FIG. 8B) A closer view of the 500 mL suspension bioreactor and measuring probes.

FIGS. 9A-C: Process Control Techniques Used to Control Temperature, Dissolved Oxygen (DO) Level, and pH of the 500 mL bioreactor. Temperature control (FIG. 9A) at 37° C. was accomplished using a PID controller with a proportional gain of 50 and integral and derivative times of 0.03 and 1.5, respectively. DO level (FIG. 9B) was controlled at 14.7% of dissolved oxygen (70% air saturation) using a proportional controller with a gain of 45. pH control (FIG. 9C) at 7.3 was accomplished using a proportional controller with a gain of 30.

FIGS. 10A-B: Level of Nutrients and Metabolites in a Semi-Fed Batch Mode of Culture in 125 mL and 500 mL Suspension Bioreactors. Shown are the level of nutrients (glucose and glutamine) and metabolites (lactate and ammonia) in (FIG. 10A) 125 mL suspension bioreactors, and (FIG. 10B) 500 mL computer-controlled bioreactors. Bioreactors were run in semi-fed batch mode, where the cultures were fed every 5 days (shown by green arrows) by replacing 40% of the spent medium with fresh PPRF-h2 medium. Samples were taken every other day over the course of 20 days. The level of nutrients and toxic metabolic by-products were measured using a NOVA Bioprofile analyzer.

DESCRIPTION OF THE ILLUSTRATIVE EMBODIMENTS

Figure 1:
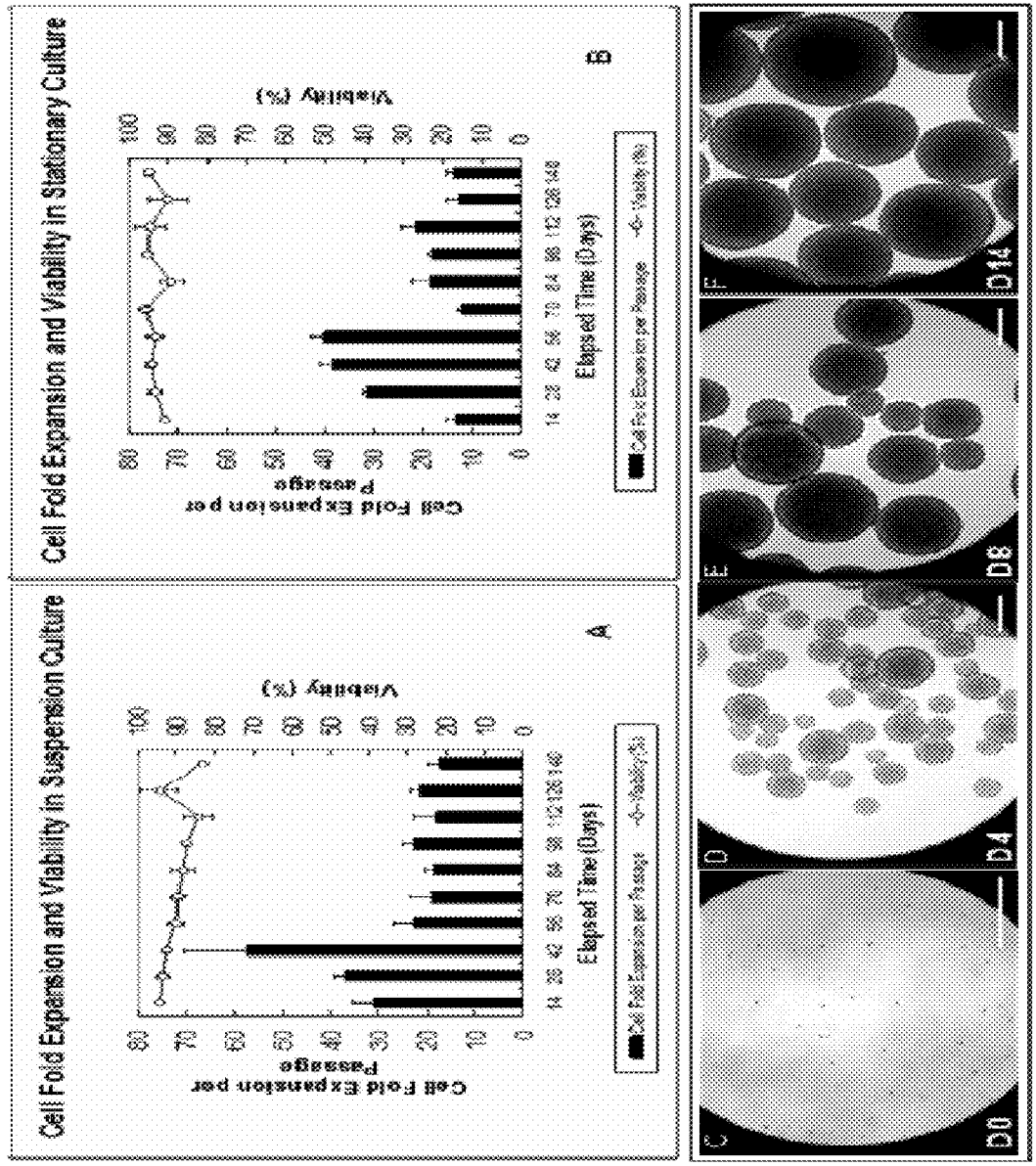
FIGS. 1A-F: Serial Subculturing of Telencephalon Derived hNPCs (140 days). Shown are cell fold expansion and viability (%) of the cells serially subcultured every 14 days using PPRF-h2 medium in (FIG. 1A) duplicate 125 mL suspension bioreactors, and (FIG. 1B) duplicate T-25 flasks. Photomicrographs demonstrate the cells grown in 125 mL bioreactors (FIG. 1C) immediately following inoculation, (FIG. 1D) 4 days post-inoculation, (FIG. 1E) 8 days post-inoculation, and (FIG. 1F) 14 days post-inoculation. Scale bars represent 250 µm.

In this study, the inventors report successful production of hNPCs in large-scale computer-controlled bioreactors using their modified serum-free growth medium. Growth kinetics, hydrodynamic effects, oxygen transfer, and feasibility of the scale-up process were first studied in standard smaller-scale bioreactors. In addition, aggregate size control, growth characteristics, and multipotentiality of the cells grown in the larger-scale suspension bioreactors operating at controlled physiological conditions were investigated.

I. NEURAL MEDIA

PPRF-h2 is a serum-free growth medium that has been modified from PPRF-m4 medium originally developed for the expansion of murine neural precursor cells (NPCs). PPRF-h2 is prepared by adding different cytokines in a mixture of commercially available basal media, as described below.

A. Components

Basal Media/Nutrients. Basal media will comprise, in one example, Dulbecco's modified Eagle's medium (DMEM). 5×DMEM stock solution is prepared by dissolving one packet of powdered DMEM (Gibco, 12100-046) in 200 mL of cell culture grade water. The reconstituted DMEM is then filtered through a 0.22 µm filter using a sterile Pyrex glass bottle and stored at 4° C. for a period of maximum two months.

Nutrients can be provided by Ham's F12 Nutrient Mixture (F12) or other media mix. 10× F12 stock solution is prepared by dissolving one packet of powdered F12 (Gibco, 21700-026) in 100 mL of cell culture grade water. The reconstituted F12 is then filtered through a 0.22 µm filter using a sterile Pyrex glass bottle and stored at 4° C. for a period of maximum two months.

Glutamine (20 mM stock solution). A 20 mM sterile glutamine stock solution (Gibco, 25030-081) is aliquoted into 10 mL aliquots, and stored at −20° C. Prior to use, an aliquot is thawed in a 37° C. water bath, and then agitated to completely dissolve the glutamine precipitated during the freeze-thaw process. The reminder is covered in aluminium foil and stored at 4° C. for a maximum of two months.

Sodium Bicarbonate (7.5% stock solution). A 7.5% sodium bicarbonate stock solution is prepared by dissolving 7.5 g of sodium bicarbonate (Sigma, S-5761) into 100 mL of cell culture grade water. The stock solution was then filtered through a 0.22 µm filter and stored at −20° C. in 20 mL aliquots. Prior to use, an aliquot was thawed in a 37° C. water bath, and then agitated to completely dissolve the sodium bicarbonate precipitated during the freeze-thaw process. The remainder was placed at 4° C. for future use.

Hepes (1M stock solution). A 1.0 M Hepes stock solution is prepared by dissolving 23.8 g of Hepes (Sigma, H-4034) into 80 mL of cell culture grade water. Then, more water is added to the dissolved solution of Hepes until a total volume of 100 mL is reached. The stock solution is filtered through a 0.22 µm filter, aliquoted and stored at 4° C.

Recombinant Human EGF (20 mg/L). A 20 mg/L stock solution of EGF is prepared by reconstituting 100 µg of lyophilized EGF (PeproTech Inc., 100-15) in 5.0 mL of sterile 1.0 mg/mL bovine serum albumin (BSA) previously prepared in 1×PBS solution and adjusted to a pH of 7.2-7.4. The EGF stock solution is then aliquoted into 500 µL aliquots and stored at −80° C. Prior to use, an aliquot is thawed, and the remainder is placed at −80° C. for future use.

Recombinant Human bFGF (20 mg/L). A 20 mg/L stock solution of bFGF is prepared by reconstituting 25 µg of lyophilized bFGF (R&D Systems, 233-FB) in 1250.0 µL of sterile 1.0 mg/mL BSA previously prepared in 1×PBS solution and adjusted to a pH of 7.2-7.4. The bFGF stock solution is then aliquoted into 200 µL aliquots and stored at −80° C. Prior to use, an aliquot is thawed, and the remainder is placed at −80° C. for future use.

Recombinant hLIF (10 mg/L). A purchased 10 mg/L vial of hLIF (Chemicon International, LIF1010) is aliquoted into 100 µL aliquots, and stored at 4° C.

Dehydroepiandrosterone (DHEA) (10 mM stock solution). A 10 mM stock solution of DHEA is prepared by reconstituting 28.842 mg of DHEA (Steraloids Inc., A8500-000) in 10 mL of 100% ethanol. The DHEA stock solution is then stored at −20° C. for future use.

Heparin (5 g/L Stock Solution). A 5 g/L sterile heparin stock solution is prepared by dissolving 0.05 g of heparin (Sigma, H-3149) into 10 mL of cell culture grade water. The stock solution is then filtered through a 0.22 µm filter and stored at 4° C. for future use.

Hormone Mixture. Another component is a hormone mixture, which may include the following:

Glucose (30% stock solution). A 30% glucose stock solution is prepared by dissolving 30 g of glucose (Sigma, G-7021) into 100 mL of cell culture grade water. The stock solution is then filtered through a 0.22 µm filter and stored at −20° C. in 20 mL aliquots. Prior to use, an aliquot is thawed in a 37° C. water bath, and then agitated to completely dissolve the sodium bicarbonate precipitated during the freeze-thaw process. The remainder is discarded.

Apo-Transferrin (83.33 g/L Stock Solution). A 83.33 g/L apo-Transferrin stock solution is prepared by dissolving 250 mg of apo-Transferrin (Sigma, T-2252) in 3 mL of cell culture grade water.

Insulin (23 g/L Stock Solution). A 23 g/L insulin stock solution is prepared by adding 230 mg of insulin from bovine pancreas (Sigma, 1-5500) into 10 mL of 0.1 N HCl and vortexed to completely dissolve the insulin. The insulin stock solution is freshly prepared during preparation of hormone mixture. The tubes containing insulin vial and stock solution are washed using 40 mL of cell culture grade water and added to the bottle which is provided for hormone mixture preparation.

Putrescine (9 g/L Stock Solution). A 9 g/L putrescine stock solution is prepared by dissolving 90 mg of putrescine (Sigma, P-7505) in 10 mL of cell culture grade water. The tube containing putrescine stock solution is washed by 10 mL of cell culture grade water which is then added to the bottle which is provided for hormone mixture preparation.

Selenium (3 mM Stock Solution). A 3 mM selenium stock solution is prepared by dissolving 1 mg of selenium (Sigma, S-9133) in 1.93 mL of sterile cell culture grade water. The stock solution is then stored at −20° C.

Progesterone (2 mM Stock Solution). A 2 mM progesterone stock solution is prepared by dissolving 1 mg of progesterone (Sigma, P-6149) in 1.59 mL of 0.95% ethanol. The stock solution is then stored at −20° C.

B. Medium Preparation

Hormone Mixture. The following protocol can be used to make 1.0 L of hormone mixture:

(i) Using a 1000 mL graduated cylinder, 737.00 mL of cell culture grade water is measured and placed into a sterile 1000 mL glass bottle.

(ii) Using a pipette, the following supplements are added into the bottle:

a. 100 mL of 5×DMEM
b. 50 mL of 10× F12
c. 20 mL of 30% glucose stock solution
d. 15 mL of 7.5% sodium bicarbonate stock solution
e. 5 mL of 1 M Hepes stock solution
f. 3 mL of 83.33 g/L apo-transferrin stock solution
g. 10 mL of 23 g/L insulin stock solution
h. 40 mL of cell culture grade water after washing the tubes containing insulin
i. 10 mL of 9 g/L putrescine stock solution
j. 10 mL cell culture grade water after washing the tube containing putrescine stock solution
k. 90 µL of 3 mM selenium stock solution
l. 90 µL of 2 mM progesterone stock solution The prepared hormone mixture is filtered through a 0.22 µm filter into a sterile Pyrex glass bottle. The hormone mixture is aliquoted into 40 mL aliquots and stored in a frozen state. Prior to use, an aliquot is thawed in a 37° C. water bath, and then agitated to completely dissolve the precipitated components during the freeze-thaw process. The reminder is discarded.

TABLE 1

Components Used to Produce 1.0 L of Hormone Mixture

| # | Component | Supplier, Cat # | Final Conc. | Unit | Amount |
|---|---|---|---|---|---|
| 1 | Water (Cell Culture Grade) | | | mL | 787.00 |
| 2 | DMEM (5x stock solution) | Gibco 12100-046 | 0.5x | mL | 100.00 |
| 3 | F-12 (10x stock solution) | Gibco 21700-026 | 0.5x | mL | 50.00 |
| 4 | Glucose (30% stock solution) | Sigma, G-7021 | 6 g/L | mL | 20.00 |
| 5 | sodium bicarbonate (7.5% stock solution) | Sigma S-5761 | 1.125 g/L | mL | 15.00 |
| 6 | Hepes (1M stock solution) | Sigma H-4034 | 5 mM | mL | 5.00 |
| 8 | apo-transferrin (83.33 g/L stock solution) | Sigma, T-2252 | 0.25 g/L | mL | 3.00 |
| 9 | Insulin (23 g/L solution in 0.1N HCL) | Sigma, I-5500 | 0.23 g/L | mL | 10.00 |
| 10 | Putrescine (9 g/L Stock Solution) | Sigma, P-7505 | 0.09 g/L | mL | 10.00 |
| 11 | Selenium (3 mM stock solution) | Sigma, S-9133 | 0.27 µM | mL | 0.09 |
| 12 | Progesterone (2 mM stock solution) | Sigma, P-6149 | 0.18 µM | mL | 0.09 |
| | Total | | | mL | 1000.180 |

Medium Preparation. The following protocol is used to make 1.0 L of PPRF-h2 growth medium.

(i) Using a 1000 mL graduated cylinder, 729.00 mL of cell culture grade water is measured and placed into a sterile 1000 mL glass bottle.

(ii) Using a pipette, the following supplements are added into the bottle:
 a. 90 mL of 5×DMEM
 b. 45 mL of 10× F12
 c. 5 mL of 20 mM glutamine solution
 d. 21.5 mL of 7.5% sodium bicarbonate stock solution
 e. 4.4 mL of 1 M Hepes stock solution
 f. 100 mL of hormone mixture
 g. 1.0 mL of 20 mg/L recombinant human EGF
 h. 1.0 mL of 20 mg/L recombinant human bFGF
 i. 1.0 mL of 10 mg/L recombinant hLIF
 j. 0.1 mL of 10 mM DHEA (iii) 2.0 g of BSA is weighted, added into the bottle, and allowed to dissolve at room temperature.

(iv) Using a pipette, the following supplements are added into the bottle:
 a. 1 mL of 1000× lipid concentrate
 b. 1 mL of 5 g/L heparin stock solution (v) The prepared medium is filtered through a 0.22 µm filter, which is previously blocked by 0.2% BSA solution. The growth medium is stored at 4° C. in dark for a period of maximum two weeks.

TABLE 2

Components to Prepare 1.0 L of PPRF-h2 Growth Medium

| # | Component | Supplier, Cat # | Final Conc. | Unit | Amount |
|---|---|---|---|---|---|
| 1 | Water (Cell Culture Grade) | | | mL | 729.00 |
| 2 | DMEM (5x stock solution) | Gibco 12100-046 | | mL | 90.00 |
| 3 | F-12 (10x stock solution) | Gibco 21700-026 | | mL | 45.00 |
| 4 | Glutamine (20 mM stock solution) | Gibco 25030-081 | | mL | 5.00 |
| 5 | sodium bicarbonate (7.5% stock solution) | Sigma S-5761 | | mL | 21.50 |
| 6 | Hepes (1M stock solution) | Sigma H-4034 | | mL | 4.40 |
| 7 | Hormone Mixture * | | | mL | 100.00 |
| 8 | Recombinant Human EGF (20 mg/L) | PeproTech Inc., 100-15 | 20 µg/L | mL | 1.00 |
| 9 | Recombinant Human bFGF (20 mg/L) | R&D System 233-FB | 20 µg/L | mL | 1.00 |
| 10 | Recombinant Human LIF (10 mg/L) | Chemicon International LIF1010 | 10 µg/L | mL | 1.00 |
| 11 | DHEA (10 mM Stock Solution) | Steraloids Inc. A8500-000 | 1 µM | mL | 0.10 |
| 12 | Bovine Serum Albumin | Sigma, A-9418 | 2 g/L | G | 2.00 |
| 13 | Lipid concentrate (1000x) | Gibco 11905 | 1x | mL | 1.00 |
| 14 | Heparin (5 g/L Stock Solution) | Sigma H-3149 | 2 g/L | mL | 1.00 |
| | Total | | | mL | 1000.0 |

* The components used to prepare 1.0 L of hormone mixture are shown in Table 1.

II. CELLS AND ISOLATION

A. Cell Types

The present invention may be utilized with a variety of different cell types that are generally referred to as neural precursor cells, or NPCs. Specific examples of NPCs are those obtained from forebrain (e.g., telencephalon), ventral mesencephalon, brain stem or spinal cord.

Neural stem cells may be described as those cells which exhibit one or more of the following characteristics: (1) derived from the fetal or adult central nervous system, or outside the fetal or adult central nervous system, or the developing embryo (2) retain the capacity to self-renew, (3) can undergo asymmetric division to produce cells which have more restricted potential (i.e. progenitor cells or specialized cells), (4) have the potential to generate the primary specialized cell types of the central nervous system including neurons, astrocytes, and oligodendrocytes (Gage, 2000). There is no unique cell marker for neural stem cells but they can be positively stained for the intermediate filament proteins nestin and vimentin, as typical neuroepithelial markers. CD-133 has been also suggested as one potential surface marker for neural stem cells (Coskun et al., 2008). Neural progenitor cells are cells that have limited proliferation capacity, and are already committed to a neuronal or glial fate. Neural progenitor cells can only produce one or two main cell types of the central nervous system. The committed neural progenitor cells that give rise to neurons are named neuroblasts and those that give rise to different types of glial cells are called glioblasts. The term "blasts" indicate that these cells are still capable of division (Doetsch, 2003). Early committed neural progenitor cells can stain positively for nestin or vimentin but they also show immunoreactivity for neuronal markers such as microtubule associated protein (MAP)-5. More committed neural progenitor cells do not stain for the neuroepithelial cell marker nestin (Buc-Caron, 1995). The cumulative term "precursor cells" is used to refer to neural stem cells and neural progenitor cells collectively (Ostenfeld and Svendsen 2004; Svendsen et al. 1999; Weiss et al. 1996).

B. Isolation Procedures

Human neural precursor cells may be isolated from the forebrain (e.g., telencephalon), ventral mesencephalon, brain stem or spinal cord of 6 to 13 weeks postconception fetuses using the protocols developed at the Queen Elizabeth II Health Sciences Centre under strict ethical guidelines (Mendez et al. 2000, 2002, 2005). The brain stem includes tissue underneath the rhombencephalic flexure and inferior to the ventral mesencephalon. The isolated tissues are dissected under sterile conditions. Single cell suspensions of each of these tissue types may be prepared by first rinsing the tissues in 0.05% deoxyribonuclease (DNase)/Pharmaceutical Production Research Facility (PPRF)-h2 medium (Mukhida et al. 2007), incubating them in 0.25% trypsin (Sigma-Aldrich, St. Louis, Mo.)-ethylenediaminetetra-acetic acid (EDTA) at 37° C. for 20 minutes, rinsing them again in 0.05% DNase (Sigma-Aldrich)/PPRF-h2, and mechanically dissociating them using a 1 mL and 200 µL Eppendorf pippetter until uniform cell suspensions are achieved. Tissue culture plates (including 25 cm² plates) containing PPRF-h2 expansion medium may be used to expand the cells with a 50% medium exchange performed every 4 days. After two weeks, the neurospheres are harvested, centrifuged at 1,500 rotations per minute for 5 minutes, and the pellets are incubated in 0.25% trypsin (HyClone, Logan, Utah) at 37° C. for 20 minutes. After rinsing the neurospheres with 0.05% DNase/PPRF-h2, they are mechanically dissociated into single cell suspensions and placed in expansion medium (passage level 1). The cells are now ready to be serially subcultured in PPRF-h2 growth medium.

II. BIOREACTORS FOR NON-ANCHORAGE-DEPENDENT CELL CULTURE

A. Bioreactors

The present invention can take advantage of the readily available bioreactor technology. As used herein, a "bioreactor" refers to any apparatus that can be used for the purpose of culturing cells. Bioreactors have been widely used for the production of biological products from both anchorage-independent and anchorage dependent mammalian cells. Microcarrier cell culture in stirred tank bioreactor provides very high volume-specific culture surface area and has been used for the production of viral vaccines (Griffiths, 1986). Furthermore, stirred tank bioreactors have industrially proven to be scalable. Standard 125 mL or 250 mL spinner flasks (Corning) as well as 500 mL or 1000 mL bioreactors (Wheaton) are among the stirred tank bioreactors effectively used to produce mammalian cells (Kallos and Behie (Kallos and Behie 1999; Kallos et al. 1999; Sen et al. 2001; Sen et al. 2002a; Sen et al. 2002b; Youn et al. 2005; Youn et al. 2006; Gilbertson et al. 2006). The multiplate CellCube™ cell culture system manufactured by Corning-Costar also offers a very high volume specific surface area. Cells grow on both sides of the culture plates hermetically sealed together in the shape of a compact cube. Unlike stirred tank bioreactors, the CellCube™ culture unit is disposable. Another example of a bioreactor that may be employed in the present invention is a Wave Bioreactor®. The Wave Bioreactor® can be a Wave Biotech® model20/50EH.

Animal and human cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth). Large scale suspension culture of mammalian cells has been developed using instrumentation and controls adapted, along with the design of the fermentors, from related microbial applications. However, acknowledging the increased demand for contamination control in the slower growing mammalian cultures, improved aseptic designs have been implemented, improving dependability of these reactors. Instrumentation and controls are basically the same as found in other fermentors and include agitation, temperature, dissolved oxygen, and pH controls. More advanced probes and autoanalyzers for on-line and off-line measurements of turbidity (a function of particles present), capacitance (a function of viable cells present), glucose/lactate, carbonate/bicarbonate and carbon dioxide are available.

Two suspension culture reactor designs are most widely used in the industry due to their simplicity and robustness of operation—the stirred reactor and the airlift reactor. The stirred reactor design has successfully been used on a scale of 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

Most large-scale suspension cultures are operated as batch or semi-fed-batch processes because they are the most straightforward to operate and scale up. However, continuous processes based on chemostat or perfusion principles are available.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a "fed-batch" process is still a closed system because cells, products and waste products are not removed. A semi-fed batch process refers to the case where key nutrients are periodically fed to an otherwise batch system following the removal of a percentage of the spent medium. Perfusion of fresh medium through the culture can be achieved by retaining the cells with a variety of devices (e.g. fine mesh spin filter, hollow fiber or flat plate membrane filters, settling tubes). Spin filter cultures can produce cell densities of approximately $5 \times 10^7$ cells/mL. Particular methods for semi-fed-batch processes are provided in the Examples below.

A true open system and the simplest perfusion process is the chemostat in which there is a continuous inflow of medium and a continuous outflow of cells and products. Culture medium is fed to the reactor at a predetermined and constant rate which maintains the dilution rate of the culture at a value less than the maximum specific growth rate of the cells (to prevent washout of the cell mass from the reactor). Culture fluid containing cells and cell products and byproducts is removed at the same rate.

B. Culture Considerations

Aggregates and shear forces. Human NPCs grow in the form of aggregates of cells called neurospheres in serum-free growth medium, and the size of an aggregate increases over time in culture. Extremely large aggregates develop necrotic cores due to diffusional limitations which prevent adequate quantities of essential nutrients and/or oxygen from reaching the cells at the centre. These issues can be addressed, in suspension bioreactors, by agitation, e.g., with a rotating magnetic impeller. While this provides well-mixed, homogeneous conditions within the vessel, the cells grown in these bioreactors are subjected to shear stress created fluid vortices, called eddies.

However, the magnitude of the shear can be manipulated in culture by controlling the agitation rate in the bioreactor. An appropriate agitation rate (and thus shear level) is one that does not harm the cells, and is able to control the diameter of an aggregate to below that at which necrosis is initiated. An exemplary agitation rate of between 50 and 100 rpm, more specifically 80-90 rpm, and in particular 85 rpm, is provided. Alternatively, conditions that generate shear forces between 35 and 80 Pa are desired.

Oxygenation. Maintaining oxygen transfer rates at acceptable levels in suspension bioreactors is crucial to achieve a successful cell production system, a problem exacerbated by the low solubility of oxygen (0.22 mM at 37° C. in an air-saturated aqueous solution). Surface aeration (gas diffusion through the culture surface) and sparging (direct aeration within the growth medium) are the most common methods of supplying oxygen to the cells grown in culture. Due to simplicity, surface aeration is often the method of choice to meet the oxygen demand for cultures of less than one liter in volume (Butler, 2004). The inventors have used surface aeration at a particular agitation rate to maintain the oxygen transfer rate (OTR) in suspension culture at an acceptable level, and this is compatible with the shear forces and rpm's described above.

Process control. In order for hNPCs to be approved for use in clinical settings, they have to be generated in a reproducible manner under controlled, standard conditions. Using measuring probes for dissolved oxygen (DO), pH, and temperature, the inventors apply standard process control techniques to monitor and properly control the environmental parameters of hNPC cultures.

Temperature control (37° C.) can be accomplished using a Proportional-Integral-Derivative controller (PID) controller with a proportional gain of 50 and integral and derivative times of 0.03 and 1.5, respectively. pH control (7.3) can be accomplished using a proportional controller with a gain of 30. It is important to note that PPRF-h2 contains buffers to facilitate pH control. Dissolved oxygen level may be controlled at 14.7% of dissolved oxygen (equivalent to 70% air saturation) using a proportional controller with a gain of 45.

Semi-Fed Batch Process. Considering the doubling time of about 3-4 days for hNPCs grown in PPRF-h2 medium, the inventors choose to incorporate a semi-fed batch mode of culture to extend hNPC expansion in culture while maintaining essential nutrients (e.g., glucose and glutamine) and toxic metabolic by-products (e.g., lactate and ammonia) at acceptable levels. Moreover, this strategy ensures the maintenance of growth factors and amino acids at adequate levels.

IV. EXAMPLES

The following examples are included to demonstrate particular embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Development of PPRF-h2 Serum-Free Growth Medium

PPRF-h2 is a serum-free growth medium that has been modified from PPRF-m4 medium originally developed for the expansion of murine neural precursor cells (NPCs). PPRF-h2 is prepared by adding different cytokines including recombinant human epidermal growth factor (EGF), recombinant human basic fibroblast growth factor (bFGF), and recombinant human leukemia inhibitory factor (hLIF) and other growth supplements to a mixture of commercially available basal media and nutrients (DMEM/F12).

All components of PPRF-h2 growth medium are non-animal derived components except for heparin, albumin, and insulin. The heparin used in the PPRF-h2 medium is derived from porcine intestinal mucosa, and already has Food and Drug Administration (FDA) approval for use in clinical applications (e.g., injectable anticoagulant for treatment of thrombosis) (De Caterina et al., 2007). Albumin can be human or bovine serum albumin, and in particular contains only isolated serum albumins, i.e., with no significant amounts of other serum components. Insulin can be recombinant human insulin or bovine pancreas-derived insulin. Replacing the animal derived insulin and albumin with respective human derived components is feasible and does not compromise hNPC growth in culture. Therefore, PPRF-h2 medium has the potential to be made using components derived exclusively from non-xenogenic sources, thereby alleviating concerns (e.g., infectious agents, immunogenicity) associated with the use of animal derived products for clinical applications.

PPRF-h2 growth medium has been effectively used to produce large quantities of human NPCs obtained from different regions of the fetal brain including the forebrain, ventral mesencephalon, brain stem, and spinal cord in both stationary cultures and suspension bioreactors. Human NPC expansion in PPRF-h2 growth medium allows production of large numbers of cells that have been proven to be clinically effective in treatment of animal models of Parkinson's disease (Mukhida et al., 2006), Huntington's disease (unpublished data), and neuropathic pain (Mukhida et al., 2007).

Figure 2:
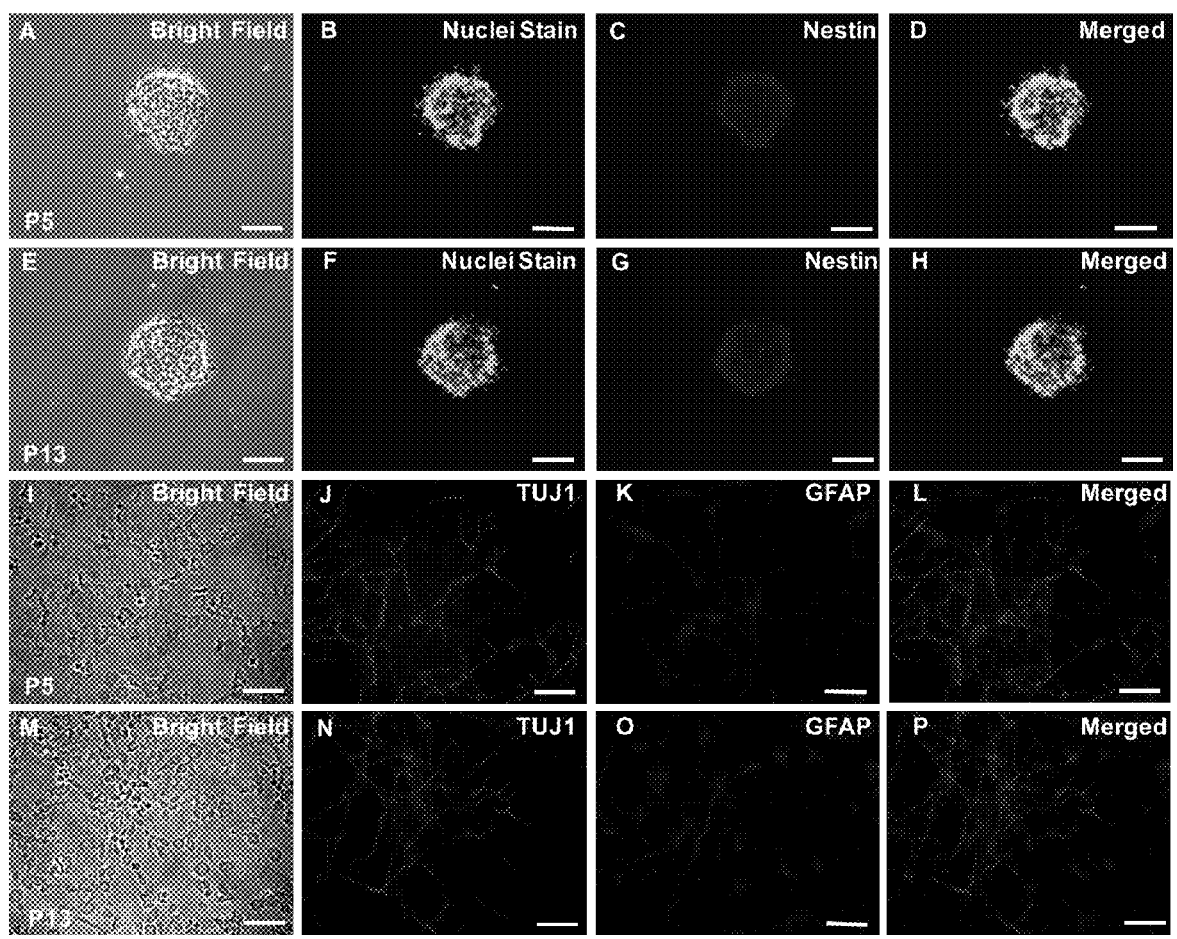
FIGS. 2A-P: Immunocytochemical Analyses of the Undifferentiated Bioreactor-Expanded hNPCs Grown in 125 mL Bioreactor and Multi-lineage Differentiation into Neuronal and Astroglial Phenotypes. Shown are (FIG. 2A) brightfield image of one hNPC aggregate taken from a 125 mL bioreactor at passage 5 and stained for (FIG. 2B) nuclei marker (YOPRO-1; green), (FIG. 2C), nestin (blue) and (FIG. 2D) both nestin (blue) and YOPRO-1 (green). Also, shown are (FIG. 2E) brightfield image of one hNPC aggregate taken from a 125 mL bioreactor at passage level 13 and stained for (FIG. 2F) YOPRO-1 (green), (FIG. 2G), nestin (blue) and (FIG. 2H) both nestin (blue) and YOPRO-1 (green). Photomicrograph (FIG. 2I) shows a brightfield image of differentiated hNPCs taken from a 125 mL bioreactor at passage 5 and stained for (FIG. 2J) neuronal marker TUJ1 (red), (FIG. 2K) cell nuclei marker (DAP1; blue), and (FIG. 2L) co-stained for DAP1 (blue) and TUJ1 (red). Photomicrograph (FIG. 2M) shows a brightfield image of differentiated hNPCs taken from a 125 mL bioreactor at passage 13 and stained for (FIG. 2N) neuronal marker TUJ1 (red), (FIG. 2O) cell nuclei marker (DAP1; blue), and (FIG. 2P) co-stained for DAP1 (blue) and TUJ1 (red). Scale bars in FIGS. 2A-H are 100 µm. Scale bars in FIGS. 2I-P are 50 µm.

Human NPCs grown in PPRF-h2 medium retain long-term proliferation activity (FIGS. 1A-F), expression for the well-know neural stem cell or neural progenitor cell marker nestin, and multipotentiality for neuronal and glial phenotypes (FIGS. 2A-P). FIGS. 1A-F demonstrate the results of long-term expansion of human NPCs obtained from the telencephalon of a 10 week post-conception fetus. The cells were serially subcultured in 125 mL standard suspension bioreactors for a period of 140 days (10 serial passages) (FIG. 1A). A parallel study was also conducted in stationary culture (T-25 flasks) (FIG. 1B). FIGS. 1C-F shows photomicrographs of the telencephalon-derived hNPCs grown in 125 mL bioreactors at passage level 13 on culture day 0, day 4, day 8 and day 14. The cells form aggregates of cells in culture, and aggregates larger than 500 μm in diameter could be observed on day 14 in suspension bioreactors.

The results of these studies showed that hNPCs maintained high proliferation activity in both stationary culture and suspension bioreactors over the entire course of the study. The viability of the cells maintained above 90% over the entire course of the study. Overall cell-fold expansions of $7.8 \times 10^{13}$ and $1.0 \times 10^{13}$ were determined for serial subculturing of the telencephalon-derived hNPCs in suspension bioreactors and stationary culture, respectively.

Immunocytochemical analysis of the undifferentiated and differentiated telencephalon-derived hNPCs was conducted at the early passage (passage level 5) and after serial subculturing for extended period in suspension bioreactors (passage level 13). Undifferentiated bioreactor-expanded hNPCs retained the ability to stain for nestin after being serially subcultured in standard suspension bioreactors (FIGS. 2A-H). When hNPCs were obtained at passage level 5 or passage level 13 from suspension bioreactors and differentiated (over the course of 10 days) on adherent substrate in the absence of growth factors (i.e., cytokine-free PPRF-h2 medium), the cells derived from either passage demonstrated comparable immunoreactivity for neuronal (TUJ1-IR) and astrocytes (GFAP-IR) markers (FIGS. 2I-P).

Figure 3:
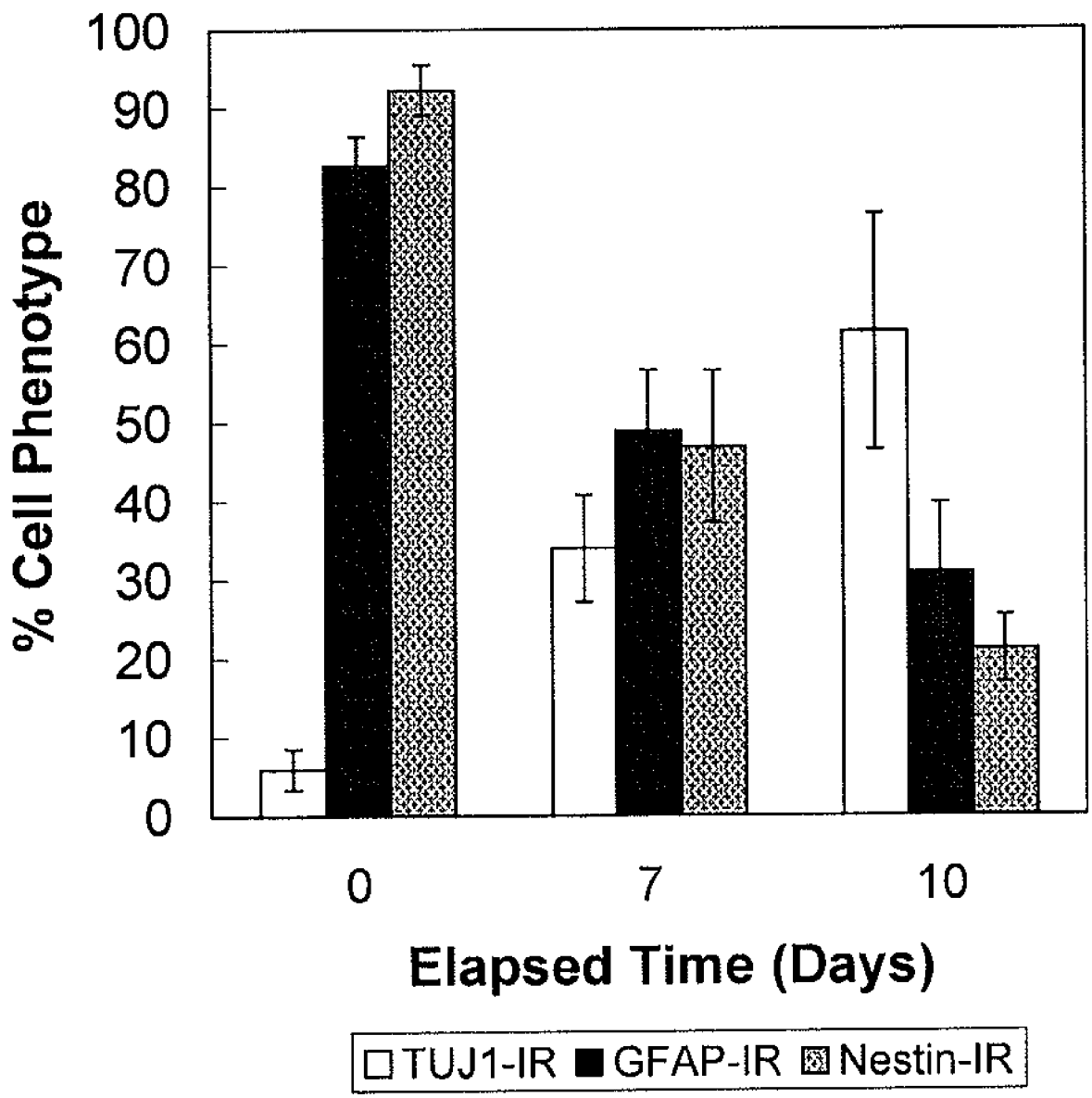
FIG. 3: Progress of Differentiation of hNPCs in the Cytokine-Free PPRF-h2. Human telencephalon-derived hNPC aggregates were taken on day 10 of Passage 12 (P12) from one 125 mL suspension bioreactor (after being serially subcultured for a period of 126 days in suspension culture), enzymatically dissociated into a single cell suspension, and plated at 20,000 cells/well into poly-D-lysine/laminin pre-coated wells on Lab-Tek chamber slides. Each well contained 200 µL of cytokine-free PPRF-h2 medium. The experiment was performed for a period of 10 days, and the number of nestin-IR, TUJ1-IR, O4-IR and GFAP-IR cells were quantified on day 0, day 7, and day 10 of the study (one slide per day). Cells co-labelled for TUJ1 and DAP1 were used to quantify TUJ1-IR cells (neurons). Measurements were performed in three separate wells of each chamber slide by scanning six random fields of the differentiated cells using a Zeiss Axiovert 200M microscope with a 40× objective.
Figure 4:
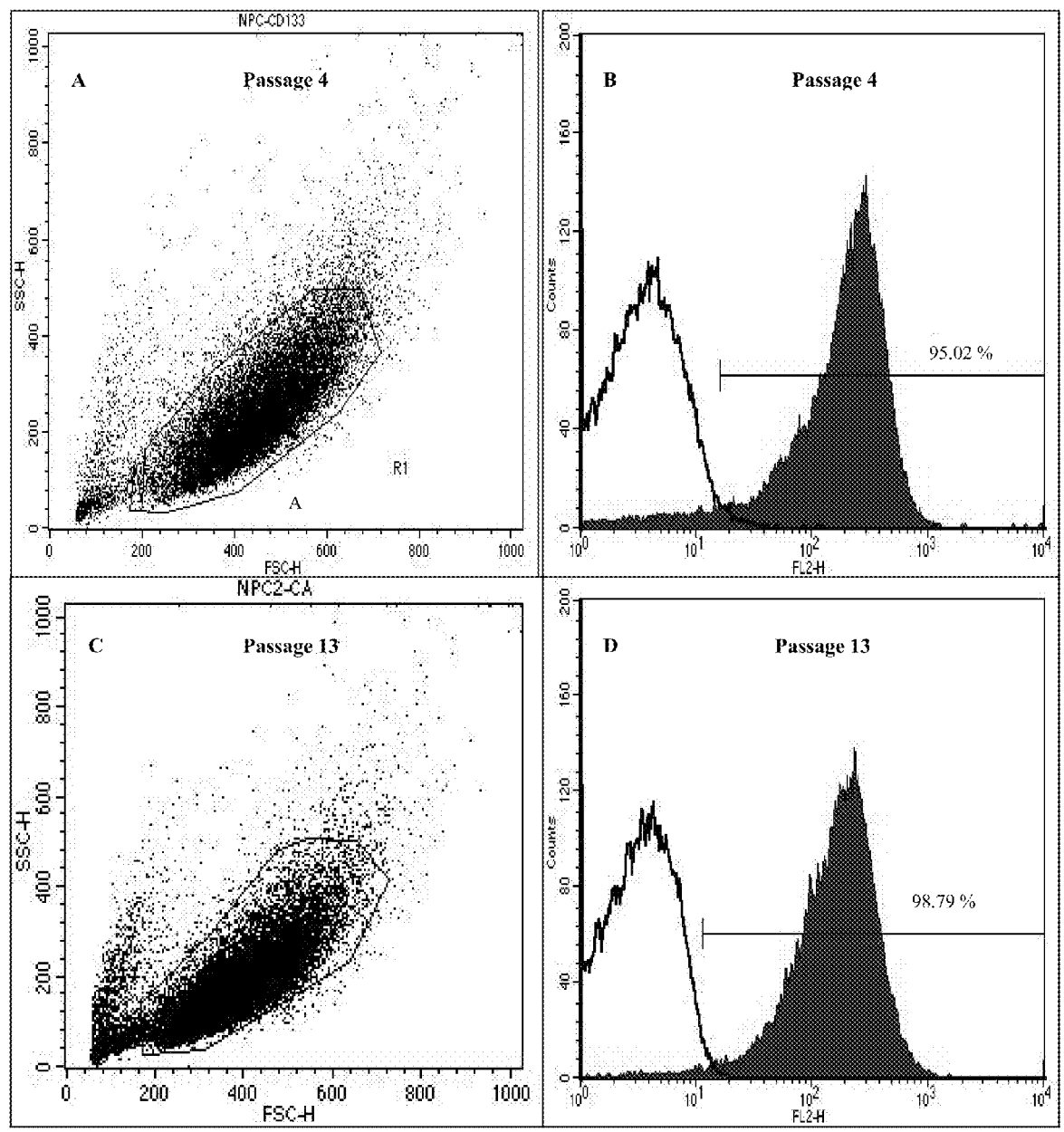
FIGS. 4A-D: FACS Analysis for Evaluation of a Population of CD133$^+$ Human NPCs after Short Term Expansion and Long-Term Expansion in PPRF-h2 Medium. Shown are forward scatter and side scatter flow cytometry dot plots of passage level 4 human NPCs grown in stationary culture (FIG. 4A), and histograms of gated passage level 4 human NPCs (FIG. 4B). Also shown are forward scatter and side scatter flow cytometry dot plots of passage level 13 human NPCs (FIG. 4C), and histograms of gated passage level 13 human NPCs (FIG. 4D). Note that the passage level 13 cells underwent expansion from passages 1-4 in stationary culture, passages 5-12 in 125 mL suspension bioreactors, and passage 13 again in stationary culture. The proportion of labelled cells exhibiting fluorescence (red histogram) greater in intensity than the negative control (white histogram) is expressed as a percentage in FIG. 4B and FIG. 4D.

Evaluation of the progress of differentiation of human NPCs following withdrawal of the cytokines from PPRF-h2 medium demonstrated that the proportion of nestin-IR cells (neural stem or progenitor cells) and GFAP-IR cells (astrocytic phenotype) decreased over time (from day 0 to day 10) whilst the proportion of TUJ1-IR cells (neuronal phenotype) increased over that same period (FIG. 3). The increase in the proportion of neurons coincided with the decrease in the proportion of nestin-IR and GFAP-IR cells. These results suggest that the neurons observed on day 10 of differentiation are derived from neuronal precursor cells exposed to the appropriate differentiation conditions (i.e., cytokine-free medium and poly-D-Lysine/laminin precoated surface). Importantly, these results demonstrate that PPRF-h2 medium supports the expansion and not the differentiation of hNPCs in culture and that differentiation can occur after withdrawal of essential growth supplements (i.e., EGF, bFGF, LIF, and DHEA).

Further characterization of hNPCs grown in PPRF-h2 growth medium using florescence activated cell sorting (FACS) demonstrated the presence of a population of $CD133^+$ cells before and after being serially subcultured for an extended period in 125 mL suspension bioreactors. CD133 is a surface marker protein selectively expressed by neurosphere initiating cells, and has been shown to be expressed by human NPCs derived from the forebrain (Piao et al., 2006). CD133 has been suggested as a potential surface marker for neural stem cells (Coskun et al., 2008; Uchida et al., 2000). The results of FACS analysis showed that approximately 95% of the cells obtained from early passage (passage level 4) cultures were $CD133^+$, which was similar to the percentage of $CD133^+$ cells (97%) obtained from the late passage (passage level 13) (including multiple passages in a suspension bioreactor) cell population (FIGS. 4A-D). These results suggest that a high percentage of the bioreactor-expanded hNPCs grown in PPRF-h2 medium are actively proliferating sphere-initiating cells.

These results demonstrate that human NPCs can be serially subcultured for extended period of time using PPRF-h2 growth medium without compromising their defining characteristics.

Example 2

Controlling the Size of hNPC Aggregates Below a Critical Threshold

Human NPCs grow in the form of aggregates of cells called neurospheres in serum-free growth medium, and the size of an aggregate increases over time in culture. Extremely large aggregates develop necrotic cores due to diffusional limitations which prevent adequate quantities of essential nutrients and/or oxygen from reaching the cells at the centre. The inventors have shown that aggregate size can be controlled using liquid shear in suspension bioreactors. The following describes how the aggregate size control has been achieved.

In suspension bioreactors, hNPCs within the culture are maintained in suspension by agitating a rotating magnetic impeller. Whereas this provides well-mixed, homogeneous conditions within the vessel, the cells grown in these bioreactors are subjected to shear stress created by the movement of the growth medium. Agitation results in the production of fluid vortices, called eddies. Eddies can be of similar size to the cells and can exert shear stresses on the suspended cells and aggregates in the bioreactor. The maximum shear can be found at the tip of the impeller (Cherry and Kwon, 1990; Sen et al., 2002a). The magnitude of the shear can be manipulated in culture by controlling the agitation rate of the impeller in the bioreactor. An appropriate agitation rate (and thus shear level) is one that does not harm the cells, and is able to control the diameter of an aggregate to below that at which necrosis is initiated. The following study demonstrates the results of hNPC aggregate size control using liquid shear in 125 mL suspension bioreactors.

To investigate the effect of liquid shear on hNPC aggregate production, hNPCs at passage level 10 were inoculated into standard 125 mL suspension bioreactors operated at 70 rpm, 100 rpm, or 130 rpm. Using the Kolmogoroff theory of turbulent eddies (Cherry and Kwon, 1990) and the Nagata correlation (Nagata 1975), the equivalent maximum shear stresses for agitation rates of 70, 100, and 130 rpm were calculated to be 0.35, 0.58, and 0.82 Pa, respectively. Duplicate bioreactors were used at each agitation rate. A growth kinetic analysis was performed for a period of 20 days in suspension culture. In addition, the manipulation of hydrodynamics as a means to control aggregate size was evaluated by determining the change in average aggregate size and the aggregate size distribution of the cells grown at each agitation rate.

Figure 5:
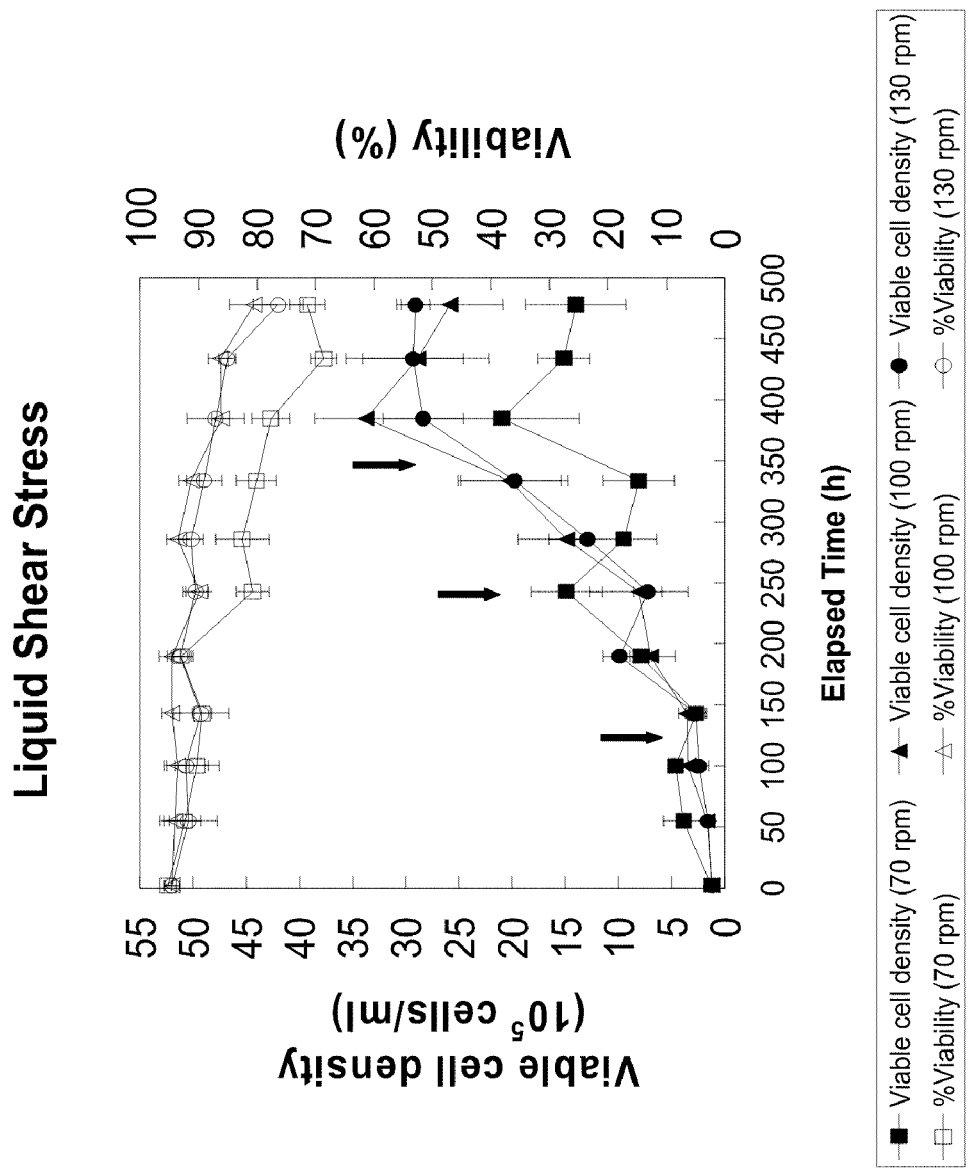
FIG. 5: Effects of Liquid Shear on the Viable Cell Density and Viability of hNPCs in Small-Scale Bioreactors (125 mL). Human telencephalon-derived NPCs were inoculated at 100,000 cells/mL into suspension bioreactors operating at 70, 100, or 130 rpm. The bioreactors were incubated at 37° C., 95% air, and 5% $CO_2$. The cells were fed every 5 days (shown by arrow) by replacing 40% of the spent medium with fresh medium. All data points represent the average of duplicate spinner flasks each counted twice. Error bars demonstrate the standard deviation for each measurement.

FIG. 5 shows the viable cell density and viability of human telencephalon-derived NPCs grown in 125 mL bioreactors at 70, 100, and 130 rpm. The cells were inoculated at 100,000 cells/mL into each bioreactor. All three agitation rates supported expansion of hNPCs, indicating that a maximum shear stress between 0.35 to 0.80 Pa may sustain expansion of these cells in small-scale suspension culture. However, the viable cell density at 70 rpm fluctuated over the course of the study, reaching a maximum viable cell density of $(2.10\pm0.73)\times10^6$ cells/mL on day 16. The highest cell concentration achieved at 100 rpm was $(3.37\pm0.49)\times10^6$ cells/mL. Moreover, the cells exhibited a doubling time (DT) of 85 hr, and maintained a viability of greater than 90% at 100 rpm.

Figure 6:
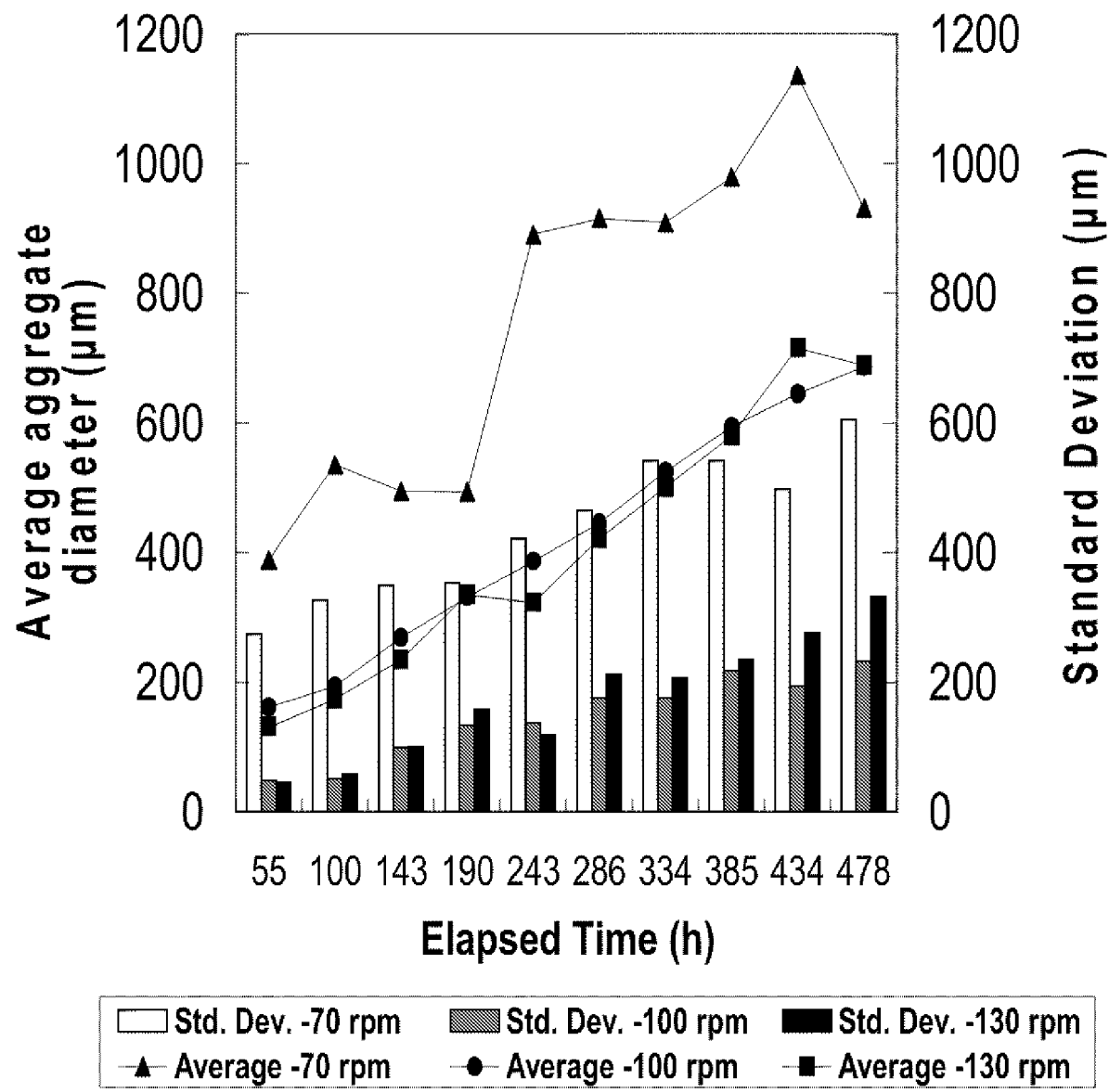
FIG. 6: Effects of Liquid Shear on Mean Aggregate Diameter in 125 mL bioreactor. All data points represent the average of duplicate bioreactors each counted twice.

The average hNPC aggregate diameter measured at each tested agitation rate in 125 mL bioreactors is shown in FIG. 6. It can be seen that at 70 rpm, aggregates larger than 400 μm could be observed by the second day of culture, while the average aggregate size at the higher agitation rates was much smaller (<200 μm) after the same time period. This trend remained over the entire course of the study. The average aggregate diameter at both 100 rpm and 130 rpm was less than 600 μm (approximately 550 μm) on day 16, while the mean diameter reached >950 μm after the same time period at 70 rpm. The measured aggregate size distribution for each tested agitation rate is shown in FIGS. 7A-D. At two days post-inoculation most of the single cells inoculated into the culture at 70 rpm formed aggregates larger than 300 μm in diameter with about 20% of the aggregates between 700 μm and 900 μm in diameter. In contrast, the majority of aggregates formed at higher agitation rates (100 and 130 rpm) were smaller than 700 μm in diameter over the entire course of the experiment. The development of extremely large aggregates is undesirable as it may result in unfavorable outcomes such as cell death due to intra-aggregate mass transfer limitations. It should be noted that the 100 rpm culture was observed to be cleaner and contained less cell debris than the 130 rpm culture.

Overall, these results demonstrated that a moderate agitation rate of 100 rpm can be effectively used to control the size of hNPC aggregates below an average diameter of 600 μm without negatively affecting the expansion and viability of hNPCs in 125 mL suspension bioreactors.

These studies have shown that the addition of measuring probes significantly changes the hydrodynamics within large-scale (500 mL) computer controlled bioreactors when compared to small scale (125 mL) suspension bioreactors. Therefore, the agitation rate in 500 mL computer-controlled bioreactor should be lowered to 85 rpm to avoid detrimental effects of high agitation rate. Yet, the agitation rate is sufficient to control hNPC aggregates size distribution below an average aggregates size of approximately 500 μm.

Example 3

Maintaining Oxygen Transfer Rates Above the Minimum Levels Required to Support hNPC Expansion Maintaining oxygen transfer rates at acceptable levels in suspension bioreactors is crucial to achieve a successful cell production system. One problem which needs addressing is the low solubility of oxygen (0.22 mM at 37° C. in an air-saturated aqueous solution). Surface aeration (gas diffusion through the culture surface) and sparging (direct aeration within the growth medium) are the most common methods of supplying oxygen to the cells grown in culture. Due to simplicity, surface aeration is often the method of choice to meet the oxygen demand for cultures of less than one liter in volume (Butler, 2004). The inventors have also used surface aeration to maintain the oxygen transfer rate (OTR) in suspension culture at acceptable level. The studies described below have been performed to ensure that surface aeration is capable of achieving this goal.

To avoid oxygen depletion in the culture, the OTR across the liquid medium should meet the oxygen demand of the cells, which can be indicated by oxygen uptake rate (OUR) for each cell type. The OTR value can be estimated through calculation of the volumetric mass transfer coefficient ($k_L a$), saturation oxygen concentration in the culture medium in equilibrium with head-space oxygen ($C_{O_2}^*$), and oxygen concentration in the bulk of culture medium ($C_{O_2}$). The overall OUR value for a particular cell line can be determined from the specific oxygen uptake rate ($q_{O_2}$) and cell density in the bioreactor.

In order to evaluate whether surface aeration was sufficient to meet the oxygen demands of hNPCs in suspension culture, the inventors performed studies aimed at determining the oxygen uptake rate and comparing with the oxygen transfer rate in these bioreactors. First, the OUR value was determined by measuring $q_{O_2}$ for a single cell suspension, small aggregates alone (smaller than 400 μm), large aggregates alone (larger than 400 μm), and a mixture of single cells and small and large aggregates in a modified bioreactor containing 250 mL of PPRF-h2 medium. The measured $q_{O_2}$ values varied between $3.03\times10^{-17}$ for large aggregates to $5.87\times10^{-17}$ mol $O_2$/cell·s for single cell suspension of hNPCs. Then, using Henry's law, the value of $C_{O_2}^*$ was calculated to be $2.25\times10^{-4}$ mol/L for the bioreactors incubated in 95% air and 5% $CO_2$. Therefore, for a worst case scenario, the minimum value for $k_L a$ was calculated to be 2.0 $h^{-1}$ to achieve a viable cell density of $3.2\times10^6$ cells/mL (small aggregates, worst case scenario) of hNPCs ($q_{O_2}$ value of $3.84\times10^{-17}$ mol $O_2$/cell·s) in a suspension bioreactor.

Since the mass transfer coefficient is significantly influenced by hydrodynamic shear, $k_L a$ values at different agitation rates were calculated using the Aunins et al. correlation (Aunins et al., 1989) in 125 mL suspension bioreactors. It was found that the $k_L a$ value at an agitation rate of 100 rpm (3.76 $h^{-1}$) was above the minimum oxygen transfer coefficient to meet the oxygen demands of hNPCs in culture.

Therefore, these studies indicate that surface aeration at an agitation rate of 100 rpm should be able to support oxygen requirements and expansion of hNPCs in suspension bioreactors.

Example 4

Process Control Techniques to Control Physiological Parameters

In order for hNPCs to be approved for use in clinical settings, they have to be generated in a reproducible manner under controlled, standard conditions. Using 500 mL suspension bioreactors (FIGS. 8A-B) with a 4-blade impeller (Wheaton, USA) and measuring probes including dissolved oxygen (DO) sensor (Broadley James Corporation), pH sensor (Mettler-Toledo), and temperature sensor (MINCO), the inventors have been able to apply standard process control techniques to monitor and properly control the environmental parameters of hNPC culture. The following procedure has been performed to achieve this goal.

The measuring probes were calibrated according to the instructions provided by Wheaton. The temperature of the bioreactor was maintained at 37° C. by controlling a heating pad located directly beneath the vessel. The agitation rate of the culture was controlled using a Micro Stir Model II Single Place stir plate (Wheaton). Based on previous studies in our laboratory involving the expansion of mNPCs (Gilbertson et al., 2006; Kallos and Behie, 1999; Kallos et al., 1999; Kallos et al., 2003; Sen et al., 2001; Sen et al., 2002a; Sen et al., 2002b), mammary epithelial stem cells (MESCs) (Youn et al., 2005), and breast cancer stem cells (BrCSCs) (Youn et al., 2006), the oxygen demand of the cells in the large-scale bioreactor was satisfied through headspace aeration using a gas mixture containing $O_2$, $CO_2$, and $N_2$. The gas mixture was supplied to the bioreactor via tubing connected to gas cylinders. Process control techniques were used to control temperature, dissolved oxygen level, and pH of the 500 mL bioreactor. Temperature control (37° C.) was accomplished using a Proportional-Integral-Derivative (PID) controller with a proportional gain of 50 and integral and derivative times of 0.03 and 1.5, respectively. pH was controlled at 7.3 using a proportional controller with a gain of 30. It is important to note that PPRF-h2 contains buffers to facilitate pH control. Dissolved oxygen level was controlled at 14.7% (equivalent to 70% air saturation) using a proportional controller with a gain of 45.

FIGS. 9A-C demonstrates temperature, dissolved oxygen, and pH control using the standard process control techniques over a period of 20 days in the 500 mL suspension bioreactors.

Example 5

Incorporating Semi-Fed Batch Mode of Culture

Considering the doubling time of about 3-4 days for hNPCs grown in PPRF-h2 medium, the inventors have incorporated a semi-fed batch mode of culture to extend hNPC expansion in culture while maintaining the level of essential nutrients (e.g., glucose and glutamine) and toxic metabolic by-products (e.g., lactate and ammonia) at acceptable levels. Moreover, this strategy ensures the maintenance of growth factors and amino acids at adequate levels.

Feeding in a semi-fed batch process is performed every 5 days by replacing 40% of the spent medium with fresh PPRF-h2 medium. The procedure is carried out as follows:

(1) The bioreactor is transferred to the biosafety cabinet.
(2) The agitation is stopped for 30 seconds to allow the free cells and aggregates to settle at the bottom of the bioreactor.
(3) Using a 10 mL pipette, 40% of the spent medium is withdrawn from the top of the culture via the side arms of the bioreactor.
(4) The bioreactor is immediately placed on a magnetic stirrer to restart the agitation.
(5) Using the 10 mL pipette, 40% fresh PPRF-h2 medium is placed back into the bioreactor via the side arms.
(6) The bioreactor is removed from the biosafety cabinet and returned to its original location where normal operating conditions of 37° C., 95% air (20% $O_2$) and 5% $CO_2$ (small standard 125 mL and 250 mL bioreactors), or 37° C., 70% air (14.7% $O_2$) and pH of 7.3 (large-scale computer controlled bioreactors) are restored.

FIGS. 10A-B shows the level of glucose, glutamine, lactate and ammonia in 125 mL bioreactors and 500 mL computer-controlled bioreactors. Human telencephalon-derived NPCs were inoculated at 100,000 cells/mL in PPRF-h2 medium. The cells were cultured using a semi-fed batch mode of culture as described before. Semi-fed batch culture resulted in nutrient and metabolite concentrations being maintained at accepted levels in both 125 mL and 500 mL bioreactors.

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.

Aunins et al., *Biotechnol. Bioeng.,* 43:1127-1132, 1989.
Bachoud-Levi et al., *Exp. Neurol.,* 161:194-202, 2000.
Bachoud-Levi et al., *Lancet Neurol.,* 5:303-309, 2006.
Bachoud-Levi et al., *Lancet,* 356:1975-1979, 2000.
Buc-Caron, M-H., *Neurobiol Dis* 2(1):37-47, 1995.
Butler, In: *Animal Cell Culture & Technology,* 2$^{nd}$ Ed., BIOS Scientific Publishers: London, 75-97, 2004.
Carpenter et al., *Exp. Neurol.,* 158:265-278, 1999.
Cherry and Kwon, *Biotechnol. Bioeng.,* 36(6):563-571, 1990.
Coskun et al., *Proc. Nat'l Acad. Sci. USA* 105(3):1026-31, 2008.
De Caterina et al., *Eur Heart J.* 28(7):880-913. Epub 2007.
Doetsch, F., *Nat Neurosci* 6(11): 1127-1134, 2003.
Dunnett and Rosser, *Brain Res. Bull.,* 72:132-147, 2007.
Dunnett and Rosser, *NeuroRx,* 1: 394-405, 2004.
Freed et al., *N. Engl. J. Med.,* 327:1549-1555, 1992.
Freed et al., *N. Engl. J. Med.,* 344:710-719, 2001.
Gage, F. H., *Science* 287(5457):1433-1438, 2000.
Gilbertson et al., *Biotechnol. Bioeng.,* 94(4):783-92, 2006.
Griffiths, In: *"Animal Cell Biotechnology,"* Spier and Griffiths (Eds.), Academic Press, London, 3:179-220, 1986
Kallos and Behie, *Biotechnol. Bioeng.,* 63(4):473-483, 1999.
Kallos et al., *Biotechnol. Bioeng.,* 65(5):589-599, 1999.
Kallos et al., *Med. Biol. Eng. Comput.,* 41(3):271-282, 2003.
Kopyov et al., *Exp. Neurol.,* 149: 97-108, 1998.
Lindvall et al., *Ann. Neurol.,* 35:72-180, 1994.
Lindvall et al., *Science,* 247:574-577, 1990.
Mendez et al., *Brain,* 128:1498-1510, 2005.
Mendez et al., *J. Neurosurg.,* 96:589-596, 2002.
Mizrahi, *Process Biochem.,* 9-12, 1983.
Mukhida et al., *Exp. Neurol.,* 198(2):582, 2006.
Mukhida et al., *Stem Cells,* 25(11):2874-2885, 2007.
Nagata, S., *Mixing. Principles and Applications*; Wiley, NY, 458, 1975.
Olanow et al., *Ann. Neurol.,* 54:403-414, 2003.
Ostenfeld et al., *Stem Cells* 22(5):798-811, 2004.

Phillips et al., In: *Large Scale Mammalian Cell Culture*, Feder and Tolbert (Eds.), Academic Press, Orlando, Fla., 1985.
Philpott et al., *Cell Transplant.*, 6:203-212, 1997.
Piao et al., *J Neurosci Res.*, 84(3):471-82, 2006.
Piccini et al., *Ann. Neurol.*, 48:689-695, 2000.
Piccini et al., *Nat. Neurosci.*, 2:1137-1140, 1999.
Rosser et al., *J. Neurol. Neurosurg. Psychiatry*, 73:678-685, 2002.
Sen et al., *Biotechnol. Prog.*, 18(2):337-345, 2002.
Sen et al., *Brain Res. Dev. Brain Res.*, 134(1-2):103-113, 2002a.
Sen et al., *Ind. Eng. Chem. Res.*, 40:5350-5357, 2001.
Storch and Schwarz, *Curr. Opin. Investig. Drugs*, 3: 774-781, 2002.
Storch et al., *Exp. Neurol.*, 170:317-325, 2001.
Suzuki et al., *Proc. Nat'l Acad. Sci. USA*, 101:3202-3207, 2004.
Svendsen et al., *J. Neurosci. Methods*, 85:141-152, 1998.
Svendsen C N et al., *Brain Pathol* 9(3):499-513, 1999.
Uchida et al., *Proc. Nat'l Acad. Sci. USA*, 97(26):14720-14725, 2000.
Vescovi et al., *Exp. Neurol.*, 156:71-83, 1999.
Weiss et al., *Trends Neurosci* 19(9):387-93, 1996.
Youn et al., *Biotechnol. Prog.*, 22(3):801-810, 2006.
Youn et al., *Biotechnol. Prog.*, 21(3):984-993, 2005.

What is claimed is:

1. A culture medium comprising, dissolved or dispersed in base culture media and water, the following components:
   (a) nutrients;
   (b) glutamine;
   (c) glucose;
   (d) heparin
   (e) Hepes;
   (f) recombinant human EGF at about 10 to about 40 µg/mL;
   (g) recombinant human bFGF about 10 to about 40 µg/mL;
   (h) recombinant hLIF at about 5 to about 25 µg/mL;
   (i) DHEA at about 0.1 to about 5 µmol/L;
   (j) serum albumin;
   (k) lipids; and
   (l) a mixture of hormones comprising apo-transferrin, insulin, putrescine, selenium and progesterone.

2. The medium of claim 1, wherein the base culture medium is DMEM.

3. The medium of claim 1, wherein nutrients comprises Ham's F12 nutrient mixture.

4. The medium of claim 1, wherein serum albumin is human or bovine serum albumin.

5. The medium of claim 1, wherein said medium is filter sterilized.

6. The medium of claim 1, wherein recombinant human EGF is present at about 20 µg/mL, recombinant human bFGF is present at about 20 µg/mL, recombinant hLIF is present at about 10 µg/mL, and/or DHEA is present at about 1 µmol/L.

7. The medium of claim 1, wherein apo-transferrin is present at about 0.01 to about 100 mg/L, insulin is present at about 0.01 to about 100 mg/L, putrescine is present at about 0.01 to about 100 mg/L, selenium is present at about 0.0001 to about 100 µM, and progesterone is present at about 0.0001 to about 100 µM.

8. The medium of claim 7, wherein apo-transferrin is present at about 10 to about 40 mg/L, insulin is present at about 10 to about 40 mg/L, putrescine is present at about 5 to about 20 mg/L, selenium is present at about 0.01 to about 1 µM, and progesterone is present at about 0.01 to about 1 µM.

9. The medium of claim 8, wherein apo-transferrin is present at about 25 mg/L, insulin is present at about 23 mg/L, putrescine is present at about 9 mg/L, selenium is present at about 0.027 µM, and progesterone is present at about 0.018 µM.

10. A bioreactor comprising at least one cell and the medium of claim 1.

11. The bioreactor of claim 10, wherein said cell is a neural precursor cell.

12. The bioreactor of claim 10, wherein said bioreactor is a dish, flask, vessel, bottle or multi-well plate.

13. A method of culturing a neural precursor cell (NPC) comprising the steps of:
    (a) providing an isolated NPC or NPC-containing population in culture medium according to claim 1 in a bioreactor; and
    (b) culturing said NPC or NPC-containing cell population under conditions that (i) produce cell aggregates having an average size of about 20-2000 µm in diameter after 4 days of culture, (ii) wherein said culture medium is maintained at a pH of about 7.0-7.8; and (iii) wherein said NPC or NPC-containing cell population is cultured in batch mode, semi-fed batch mode or perfusion mode.

14. The method of claim 13, wherein culturing comprises conditions that (i) produce cell aggregates having an average size of about 100-1000 µm in diameter after 5 days of culture, and (ii) wherein said culture medium is maintained at a pH of about 7.2-7.4.

15. The method of claim 13, wherein said NPC or NPC-containing population retains a neural stem or progenitor cell marker.

16. The method of claim 13, wherein said NPC or NPC-containing population is obtained from forebrain, ventral mesencephalon, brain stem or spinal cord.

17. The method of claim 13, wherein said NPC or NPC-containing population is passaged 1, 2, 3, 4, 5, 6, 7, 8, 9, 10, 11, 12, or 13 times.

18. The method of 13, wherein said NPC or NPC-containing population is maintained in culture for 2, 3, 4, 5, 6, 7, 8, 9, 10, 20, 25, 30, 35, 40, 45, 50, 55, 60, 65, 70, 75, 80, 85, 90, 95 100, 110, 120, 130 or 140 days.

19. The method of claim 13, further comprising inducing differentiation of said NPC or NPC-containing population.

20. The method of claim 19, wherein said NPC or NPC-containing population differentiates into a CNS cell.

21. The method of claim 19, wherein said NPC or NPC-containing population differentiates into an astrocyte(s) or a neuronal cell(s).

22. The method of claim 13, wherein said NPC or NPC-containing population is maintained at about 75-95% viability.

23. The method of claim 13, wherein said NPC or NPC-containing population is cultured in a stationary phase.

24. The method of claim 13, wherein said NPC or NPC-containing population is cultured in suspension with an agitation rate of greater than about 50 rpm and less than about 130 rpm.

25. The method of claim 24, wherein agitation is produced by a stir bar, an impeller or by movement of said bioreactor.

26. The method of claim 24, wherein said agitation rate is about 80 to about 90 rpm.

27. The method of claim 26, wherein said agitation rate is about 85 rpm.

28. The method of claim 13, wherein said NPC or NPC-containing population is cultured in about 0.1-5000 mL volume of culture medium.

29. The method of claim 28, wherein said NPC or NPC-containing population is cultured in about 100 mL, 200 mL, or 500 mL volume of culture medium.

30. The method of claim 13, wherein more than 50% of said cell aggregates have a size of between about 300 to about 700 μM between days 8 and 20 of culture.

31. The method of claim 13, wherein said cell aggregates have a mean size of between about 400 to about 600 μM.

32. The method of claim 13, wherein semi-fed batch mode comprises replacement of 30-50% of said culture medium each 3-6 days.

33. The method of claim 13, wherein said bioreactor is a dish, flask, bottle or multi-well plate.

34. The method of claim 13, wherein oxygenation of said culture medium is maintained at about 1-20% dissolved oxygen.

35. The method of claim 34, wherein oxygenation of said culture medium is maintained at about 5-20% dissolved oxygen.

36. The method of claim 13, wherein oxygenation of said culture medium is maintained at about 14% dissolved oxygen.

37. The method of claim 13, wherein cell-fold expansion per passage is 5-50 for the first 140 days.

38. The method of claim 13, wherein cell-fold expansion per passage is 10-40 for the first 140 days.

* * * * *